US008685674B2

(12) United States Patent
Sugahara et al.

(10) Patent No.: US 8,685,674 B2
(45) Date of Patent: Apr. 1, 2014

(54) CHONDROITIN SYNTHASE, METHOD FOR PRODUCING THE SAME AND METHOD FOR PRODUCING SACCHARIDE CHAIN-EXTENDED CHONDROITIN

(71) Applicant: Glytech, Inc., Kyoto (JP)

(72) Inventors: Kazuyuki Sugahara, Kyoto (JP); Hiroshi Kitagawa, Hyogo (JP)

(73) Assignee: Glytech, Inc., Kyoto (JP)

( * ) Notice: Subject to any disclaimer, the term of this patent is extended or adjusted under 35 U.S.C. 154(b) by 0 days.

(21) Appl. No.: 13/648,130

(22) Filed: Oct. 9, 2012

(65) Prior Publication Data

US 2013/0034878 A1 Feb. 7, 2013

Related U.S. Application Data

(62) Division of application No. 13/088,228, filed on Apr. 15, 2011, now Pat. No. 8,334,115, which is a division of application No. 12/010,856, filed on Jan. 30, 2008, now Pat. No. 7,947,481, which is a division of application No. 11/599,371, filed on Nov. 15, 2006, now Pat. No. 7,354,741, which is a division of application No. 10/485,395, filed as application No. PCT/JP02/07859 on Aug. 1, 2002, now abandoned.

(30) Foreign Application Priority Data

Aug. 1, 2001 (JP) ................. 2001-234112

(51) Int. Cl.
C12P 19/26 (2006.01)
C12P 19/18 (2006.01)
C12P 19/04 (2006.01)
C12N 9/10 (2006.01)
C07H 21/04 (2006.01)

(52) U.S. Cl.
USPC ............... 435/84; 435/97; 435/101; 435/193; 536/23.2

(58) Field of Classification Search
None
See application file for complete search history.

(56) References Cited

U.S. PATENT DOCUMENTS

2004/0002054 A1 1/2004 Horvitz et al.

FOREIGN PATENT DOCUMENTS

| WO | WO-00/12708 A2 | 3/2000 |
| WO | WO-00/27437 | 5/2000 |
| WO | WO-00/58473 A2 | 10/2000 |
| WO | WO-00/78961 A1 | 12/2000 |
| WO | WO-01/68848 A2 | 9/2001 |
| WO | WO-01/87321 A2 | 11/2001 |

OTHER PUBLICATIONS

Kitagawa, et al; Molecular Cloning and Expression of Glucuronyltransferase I Involved in the Biosynthesis of the Glycosaminoglycan-Protein Linkage Region of Proteoglycans; The Journal of Biological Chemistry; (1998); 273(12): 6615-6618.
Kitigawa, et al; Molecular Cloning and Expression of a Novel Chondroitin 6-0-Sulfotransferase; The Journal of Biological Chemistry (2000); 275(28): 21075-21080.
Amado, et al; Identification and characterization of large galactosyltransferase gene families: galactosyltransferases for all functions; Biochimica et Biophysica Acta (1999); 1473:35-53.
Deangelis, PL. et al., "Identification and Molecular Cloning of a Chondroitin Synthase from Pasteurella multocida Type F", J.Biol. Chem., (2000), vol. 275, No. 31, p. 24124-24129.
Funderburgh, et al; Chondroitin synthase (fragment), XP-002325419, Database Uniprot Online from bovine, 2002.
GenBank Accession No. AL554196, created Feb. 1, 2001.
International Preliminary Report on Patentability dated Apr. 30, 2003 in application PCT/JP2002/007859 (INV-80783/PCTX).
International Search Report dated Feb. 13, 2003 in application PCT/JP2002/007859 (INV-80783/PCTX).
Kitagawa, et al., "Molecular Cloning and Expression of a Human Chondroitin Synthase", J. Biol. Chem 276:38721-38726 (2001).
Kitagawa, et al; Characterization of serum B-glucuronyltransferase involved in chondroitin sulfate biosynthesis; Glycobiology (1997): 7(7):905-911.
Kitagawa, et al; Detection and Characterization of UDP-GalNAc: Chondroitin N-Acetylgalactosaminyltransferase in Bovine Serum Using a Simple Assay Method; J. Biochem (1995); 117(5): 1083-1087.
Kitagawa, et al; Regulation of chondroitin sulfate biosynthesis by specific sulfation: acceptor specificity of serum B-GalNAc transferase revealed by structurally defined oligosaccharides; Glycobiology (1997); 7(4):531-537.
Kitigawa,et al; Cloning of a Novel a2,3-Sialyltransferase That Sialylates Glycoprotein and Glycolipid Carbohydrate Groups, The Journal of Biological Chemistry (1994); 269(2): 1394-1401.
Kozak; Compilation and analysis of sequences upstream from the translational start site in eukaryotic mRNAs; Nucleic Acids Research (1984); 12(2): 857-872.
Kyte, et al; A Simple Method for Displaying the Hydropathic Character of a Protein; Mol. Biol., Academic Press Inc., London (1982); 157:105-132.
Lindahl, et al, Carbohydrate-peptide linkages in proteoglycans of animal, plant and bacterial origin, from Glycoprotiens: Their Composition, Structure and Function, (1972), Gottschalk ed, 5:491-517.

(Continued)

Primary Examiner — Iqbal H Chowdhury
(74) Attorney, Agent, or Firm — Foley & Lardner LLP

(57) ABSTRACT

A vector of the present invention has DNA encoding a protein or a product having the same effect as the protein, the protein containing an amino acid sequence from amino acid numbers 47 to 802 in SEQ. ID. NO:2. Expression of the DNA gives human chondroitin synthase. By using human chondroitin synthase, it is possible to produce a saccharide chain having a repeating disaccharide unit of chondroitin. The DNA or part thereof may be used as a probe for hybridization for the human chondroitin synthase.

2 Claims, 4 Drawing Sheets

(56) References Cited

OTHER PUBLICATIONS

Mizushima, et al; pEF-BOS, a powerful mammalian expression vector; Nucleic Acids Research (1990); 18(17); 5322.

Nadanaka, et al; Demonstration of the Immature Glycosaminoglycan Tetrasaccharide Sequence GlcAB1-3GalB1-3GalB1-4Xyl on Recombinant Soluble Human a-Thrombomodulin; The Journal of Biological Chemistry (1998); 273(50):33728-33734.

Nagase, et al, Prediction of the coding sequences of unidentified human genes, J DNA Res, (1999), 6(1):63-70.

Nawa, et al; Presence and Function of Chondroitin-4-Sulfate on Recombinant Human Soluble Thrombomodulin; Biochemical and Biophysical Research Communications (1990); 171(2): 729-737.

Niwa, et al; Efficient selection of high-expression transfectants with a novel eukaryotic vector; Gene (1991); 108: 193-199.

Oohira, et al, Molecular interactions of neural chondroitin sulfate proteoglycans in the brain development, (2000), Arch Biochem Biophysics, 374(1):24-34.

Sugahara, et al, Structure and function of oversulfated chondroitin sulfate variants, (2000), Trends Glycoscience Glycotechnology, 12(67):321-349.

Sugumaran, G. et al., "Biosynthesis of Chondroitin Sulfate", J.Biol. Chem., (1997), vol. 272, No. 22, p. 14399-14403.

Tamura, et al; Synthetic Studies of Glycosyl Serines in the Carbohydrate-Protein Region of Protoglycans; Liebigs Ann (1996); 1239-1257.

Tettamanti, et al; Purification and Characterization of Bovine and Ovine Submaxillary Mucins; Archives of Biochemistry and Biophysics (1968); 124:41-50.

Tone, et al; Characterization of recombinant human glucuronyltransferase I involved in the biosynthesis of the glycosaminoglycan-protein linkage region of proteoglycans; FEBS Letters (1999); 459:415-420.

Tsuchida, K. et al., Purification and characterization of fetal bovine serum B-N-acetyl-D-galactosaminyltransferase and B-D-glucuronyltransferase involved in chondroitin sulfate biosynthesis. Eur.J.Biochem., (1999), vol. 264, p. 461-467.

Tsukada, et al; B-Glucuronidase From *Ampullaria*. Purification and Kinetic Properties; Comp. Biochem. Physiol. (1987); 86B(3): 565-569.

US Notice of Allowance dated Aug. 31, 2012 in related U.S. Appl. No. 13/088,228.

US Notice of Allowance dated Nov. 1, 2007 in U.S. Appl. No. 11/599,371 (INV-80783/US2X).

US Notice of Allowance dated Feb. 4, 2011 in U.S. Appl. No. 12/010,856.

US Office Action dated May 1, 2007 in U.S. Appl. No. 11/599,371 (INV-80783/US2X).

US Office Action dated May 19, 2006 in U.S. Appl. No. 10/485,395 (INV-80783/USX).

US Office Action dated May 26, 2010 in U.S. Appl. No. 12/010,856.

US Office Action dated Mar. 27, 2012 in related U.S. Appl. No. 13/088,228.

Wang, et al, Site-specific mutagenesis of the human interleukin-2 gene: structure-function analysis of the cysteine residues, (1984), Science, 224:1431-1433.

Whisstock, et al, Prediction of protein function from protein sequence and structure, (2003), Quarterly Reviews of Biophysics, 36(3):307-340.

Wiggins, et al; Activity of the yeast MNN1 a-1,3-mannosyltransferase requires a motif conserved in many other families of glycosyltransferases; Proc. Natl. Acad. Sci. USA (1998); 95:7945-7950.

Fig. 1

```
Human       1   -MAARGCAWLSVLLGIVLGFVLASRLVLPRASERAGPRRASTGCRSLQAAASQAGGARGDARGAQLMPPGSDPDGGPLDRNFLFVGVWLFQKYLQ      99
C.elegans   1   MRVRSTCLMPVQRRATVTTLGIIFGFSITYYLFALSLTNPIICCGHQIGLFDYLDVIS----------------QRADADVHTRSQLPGHRR        79
Drosophila  1   ---------------------------------------------------------------------------------MAKSFLE          8

Human       100 TMWAWERTWSKTTLEKVQLLLELPDWPHLRLVDDSYPPQRKSFLVLRRLHDLLDKPIFMRADDDILKPRLENFLRSLNSSELLCIT             199
C.elegans   80  LLILVLIMIAAKYLCTLAYNELESVH---EEMPLLRIM-----EDDTMPPQKKSFHAVWNLAENMAEDHLLLRADDLLRPEELALFLRSVLSSAHILGLI   176
Drosophila  9   KPRYFSDTLGLELMARPRLVYLDLPFEGLINEDDRVHPQKKSFIILYFRFHLILLRFLKIRADDDVWMEPSKLLRFLRSILSSLGLGCLN            107

Human       200 GLGTTIEGKILELLGEHHVPHLSHVLKWPHLEGKCHILMLSRRISELHRTIQLEHEDVEGRCQLRAGLDQCVISLEQCCVSLEQYEONYKGIVIRDHNSKLIQ  299
C.elegans   177 GLGLEAEVCHILASTGSTDNYCWGGPEIVPSLLSDHLRASPHLEEFCIQHYLISHEDVELCRCIFHVGEACQHYEVQKLHNNQCALLESVAKNMLLRLKD    274
Drosophila  108 GKGNHSECHILFCHSLEPDHNLCWGGPGLTLSALLADHIPFCLKNLSLLEDHEDVESGRCQLGIPQLNYEMQYILRHNSCGRNALVTGKHRKLLEN      206

Human       300 AILTLHPNIEYQKHLNMLSRRISELLHRTIQLEHLVLASLSNT---------------------------------------EHELQIG-----       357
C.elegans   275 AILTLHPMCDHAVFRKVHLRNREIKLRBAQAKRSLSSFLSTAKAQTILR-------------------------------------------          323
Drosophila  207 AILTLHPNQABLLHAVQGLRAEMQESLLILDEKRFALLEVFPDESTYMLPSVSPESDSTKRHFQDHNILGGWHNLKIHCINWERKILTNLAS              306

Human       358 ---------HPESFMDRLQFRQREEILELLTG---IENDGCHMRGMDRORABDDIVMLRQRAETILLFDEFNVCLRGILLQFSEDLGVMRLETKFVDRY    448
C.elegans   324 ---------MTPNRLANHFTPARLNNNLFCADRVCHHTVLSIRHEMAGTLLRGEHEDAMLEWHNNYSLRGRSLEFRHLGYHRLDALHGQLVM         408
Drosophila  307 YKDKQTQRHSBELNKLVPASHDLDAGSHA---RSLAASSALKQK--KDHELAMRCHEDAIEFVWFHLQFSEDILGVMRLETKFVDRY               403

Human       449 LDALLLARKHKELLANTCEPVRRHLNLQLLSKIQFVBHELLLAQELAKRINLESGGLSFSSLLKKLVPQLLGSKSEHKELKDKLNILIFLGRFDMF       547
C.elegans   409 LDMIILWFLFKKFFPPNRTILSLMALWRRILHWQLLG---------KLRLSEGVELRANLTLIEDPTLH-------MIMPLGRAAIF              478
Drosophila  404 LDLLLLIKRYLBLLMRKYFMLLGGVRRILLWDRAIT-----GIFVKLEDFYNVTLQHLGSLEQNGLARLSHLMPSG---LLSHTQDLVEVLFLAGRLGTF  496

Human       548 VRLMGNPTCLIP---NANLKLVLINDSNPDRAKQVLMPTLVRLKPKADHQILPVSGELGERSRALATELS---FQFNNHSLLCDVQLFHLHFLLR       643
C.elegans   479 ARLAQHLKSICAELGODLAFSTIFNYSSLEMANRETIHVRAASFPVVTVIELGDVS-------LSRLFRHLETLPANALNLFTDWHFCDALKR         572
Drosophila  497 ERLRTVFRVCLLVLL--EHMHCDLLLEGSLLGDHLQHELHARHVYQQVNWIQRLSAFSRLLLLARSLYIRQEDIILFIDVDLREVLFTLGR           592

Human       644 CHANLTVGQINTILFESLLKIVYSGKVPLDN---HLLAFTQKTLFMWNYGEGFCHKKGDLVR---HGLDVSLQGHGHEDVLNKVLQAG----        731
C.elegans   573 IKSNILTNAQIVWLHLLFSLEFSHESWLENDKLLALALHYGRGHGLBTGYGLAWLVGRADWWHHGDTKILGHCKEDVFKAIKNG               660
Drosophila  593 VRMHTORELKQVLHLHFSLLQRRLGDAGGSELGETPRIDDELGELCFGCHCLVMKSDILEDINGFHKDLTHMCHEDVKFLKIRVTRQRGEL           692

Human       732 ------------LKTHSQHVLMVHLIVFCDPLHPKQLKLCHVGLKKSTYSLQQLAMWLEKNDPSYSKSSNENGSVRTA------              802
C.elegans   661 ------------LKLTVLVVVHLILCHCDEMPTAQKDLHCHGLKALASIDHLVLQIAQYT-----------                          715
Drosophila  693 ANTAELAMDYNEARFQWRLLSLARLADHTLVHLCHCLVDHLSLCDVQLFAPQHNCLGTKNHLSRLMEQLFHSSPENVQFAADFFROKQQQQQCAR       788
```

CHONDROITIN SYNTHASE, METHOD FOR PRODUCING THE SAME AND METHOD FOR PRODUCING SACCHARIDE CHAIN-EXTENDED CHONDROITIN

This application is a divisional of U.S. application Ser. No. 13/088,228, filed Apr. 15, 2011, which is a divisional of U.S. patent application Ser. No. 12/010,856, filed Jan. 30, 2008, now U.S. Pat. No. 7,947,481, issued May 24, 2011, which is a divisional of U.S. patent application Ser. No. 11/599,371 filed Nov. 15, 2006, now U.S. Pat. No. 7,354,741, issued Apr. 8, 2008, which is a divisional of U.S. patent application Ser. No. 10/485,395 filed Jan. 30, 2004, now abandoned, which is a 371 of PCT/JP2002/07859 filed Aug. 1, 2002, which claims priority of Japanese patent application No. 2001-234112 filed Aug. 1, 2001, which are incorporated herein by reference.

TECHNICAL FIELD

The present invention relates to (a) a vector having DNA encoding chondroitin synthase, (b) a method of producing chondroitin synthase, (c) a method of producing a saccharide chain having a repeating disaccharide unit of chondroitin, and (d) a probe for hybridization of chondroitin synthase.

BACKGROUND ART

Chondroitin sulfate, which is a kind of glycosaminoglycan (GAG), exists as a proteoglycan on cell surfaces and in an extra cellularmatrix, Chondroitin sulfate draws attendtion because Chondroitin sulfate plays an important role in neural network formation in the developing mammalian brain (Arch. Biochem. Biophys. 374, 24-34 (2000); Trends Glycosci, Glycothenol. 12 321-349 (2000).

Chondroitin sulfate has a straight-chained polymer structure having a repeating disaccharide unit having a glucuronic acid residue (GlcUA) and an N-acetylgalactosamine residue (GalNAc). A serine residue in a core protein is covalent-bonded with chondroitin sulfate via 4-saccharide structure (GlcUAβ1-3Galβ1-3Galβ1-4Xylβ1) peculiar thereto (Glycoproteins, ed. Gottsthalk, A. (Elsevier Science, New York), pp. 491-517 (1972); The Biochemistry of Glycoproteins and Proteoglycans; ed. Lennarz, W. J. (Plenum, New York), pp. 267-371 (1980)).

GAG is biosynthesized by sequentially transferring saccharides from UDP-sugar to a non-reducing end of a saccharide chain. It was found that (a) purification of bovine serum gave a glycosyltransferase that involves in biosynthesis of a repeating disaccharide unit of heparin/heparan sulfate, and (b) cDNA cloning revealed that a single protein of the glycosyltransferase catalyses both transferase reactions of N-acetylglucosamine residue (GlcNAc) and GlcUA.

On the other hand, a glycosyltransferase that involved in biosynthesis of the repeating disaccharide unit of chondroitin sulfate has not been cloned yet except the chondroitin synthase derived from a bacterium (J. Biol. Chem. 275, 24124-24129 (2000)). GlcUA transferase II (GlcAT-II) and GalNAc transferase II (GalNAcT-II) have been purified from avian cartilage (J. Biol. Chem. 272, 14399-14403 (1997)) and from bovine serum (Eur. J. Biochem. 264, 461-467 (1999)). However, cDNA cloning of those enzymes has not been performed yet because it is difficult to purify those enzymes to form homogeneity.

An object of the present invention is to provide (a) a vector having DNA encoding human chondroitin synthase, (b) a method of producing human chondroitin synthase, (c) a method of producing a saccharide chain having a repeating disaccharide unit of chondroitin, and (d) a probe for hybridization of human chondroitin synthase.

DISCLOSURE OF INVENTION

By searching through a human cDNA database, inventors of the present invention successfully found out a candidate DNA encoding human chondroitin synthase. The inventors accomplished the present invention by actually expressing the candidate DNA and confirming that the candidate DNA encodes finding human chondroitin synthase.

The present invention provides the followings:

(1) A vector earring one of DNA (a), (b) or (c) the DNA (b) or (c) encoding a protein having catalytic activities ($\alpha$) and ($\beta$), excluding a DNA encoding a protein at amino-acid position #1 to 802 in SEQ. ID. NO: 2):

(a) DNA encoding a protein having an amino acid sequence from amino acid numbers 47 to 802 in SEQ. ID. NO: 2;

(b) DNA that, in a stringent condition, hybridizes with the DNA (a), the DNA complementary with DNA (a), or DNA having part of a nucleotide sequence of the DNA (a) or the DNA complementary with the DNA (a);

(c) DNA encoding a protein having an amino acid sequence from amino acid numbers 47 to 802 in SEQ. ID. NO:2, wherein one or several amino acids in the amino acid sequence are substituted, deleted, inserted, or transpositioned;

($\alpha$) catalytic activity that transferase GalNAc from UDP-GalNAc to chondroitin;

(where UDP is uridine 5' diphosphate and GalNAc is N-acetylgalactosamine residue), and ($\beta$) catalytic activity that transferase GlcUA from UDP-GlcUA to chondroitin, (where UDP is uridine 5' diphosphate and GlcUA is glucuronic acid residue).

(2) The vector as set forth (1), wherein:
the DNA (a) corresponds to nucleotide numbers 633 to 2900 in SEQ. ID. NO: 1.

(3) The vector as set forth in (1) or (2), wherein:
the proteins are soluble.

(4) The vector as set forth in any one of (1) to (3), being an expression vector.

(5) A transformant whose host is transformed by a vector having any one of DNA (a) to (c), the DNA (b) or (c) encoding a protein having catalytic activities ($\alpha$) and ($\beta$):

(a) DNA encoding a protein having an amino acid sequence from amino acid numbers 47 to 802 in SEQ. ID. NO: 2;

(b) DNA that, in a stringent condition, hybridizes with the DNA (a), the DNA complementary with DNA (a), or DNA having part of a nucleotide sequence of the DNA. (a) or the DNA complementary with the DNA (a);

(c) DNA encoding a protein having an amino acid sequence from amino acid numbers 47 to 802 in SEQ. ID. NO:2, wherein one or several amino acids in the amino acid sequence are substituted, deleted, inserted, or transpositioned;

($\alpha$) catalytic activity that transferase GalNAc from UDP-GalNAc to chondroitin;

(where UDP is uridine 5' diphosphate and GalNAc is N-acetylgalactosamine residue), ($\beta$) catalytic activity that transferase GlcUA from UDP-GlcUA to chondroitin, (where UDP is uridine diphosphate and GlcUA is N-glucuronic acid residue).

(6) The transformant as set forth in (5), wherein:
the DNA (a) encodes finding from nucleotide numbers 633 to 2900 in SEQ. ID. NO: 1.

(7) The transformant as set forth in (5) or (6), wherein:
the proteins are soluble.

(8) A method for producing chondroitin synthase, the method comprising the steps of:
growing a transformant set forth in any one of (5) to (7); and
obtaining the chondroitin synthase from the trnasformant thus grown.

(9) A reagent for use in chondroitin synthesis, the reagent having an enzyme protein that has an amino acid sequence including an amino acid sequence (A) or (B) and has catalytic activities (α) and (β):

(A) amino acid sequence from amino acid numbers 47 to 802 in SEQ. ID. NO: 2;

(B) amino acid sequence from amino acid numbers 47 to 802 in SEQ. ID. NO:2, wherein one or several amino acids in the amino acid sequence are substituted, deleted, inserted, or transpositioned.

(α) catalytic activity that transferase GalNAc from UDP-GalNAc to chondroitin,
(where UDP is uridine 5' diphosphate, and GalNAc is N-acetylgalactosamine residue);

(β) catalytic activity that transferase GlcUA from UDP-GlcUA to chondroitin,
(where UDP is uridine 5' diphosphate and GlcUA is N-glucuronic acid residue).

(10) The reagent as set forth in (9), wherein:
the enzyme protein is soluble.

(11) Method for producing a saccharide chain expressed by Formula (3), the method comprising at least the step of causing a reagent to contact with GalNAc donor and a saccharide chain expressed by Formula (1), the reagent set forth in (9) or (10):

GlcUA-GalNAc-R¹     (1),

GalNAc-GlcUA-GalNAc-R¹     (3), (where GlcUA and GalNAc are as defined above, "-" indicates a glycoside linkage, R¹ is an arbitrary group).

(12) A method for producing a saccharide chain expressed by Formula (4), the method comprising at least the step of causing a reagent to contact with GlcUA donor and a saccharide chain expressed by Formula (2), the reagent set forth (9) or (10):

GalNAc-GlcUA-R²     (2),

GlcUA-GalNAc-GlcUA-R²     (4), (where GlcUA, GalNAc, and "-" are as defined above, R² is an arbitrary group).

(13) A method for producing a saccharide chain selected from saccharide chains expressed by Formulas (5) and (7) respectively, the method comprising at least the step of causing a reagent to contact with GalNAc donor, GlcUA donor and a saccharide chain expressed by Formula (1), the reagent set forth in Claim (9) or (10):

GlcUA-GalNAc-R¹     (1),

(GlcUA-GalNAc)n-GlcUA-GalNAc-R¹     (5),

GalNAc-(GlcUA-GalNAc)n-GlcUA-GalNAc-R¹     (7), (where n is an integer not less than 1, GlcUA, GalNAc, and "-" are as defined above, R¹ is an arbitrary group).

(14) A method for producing a saccharide chain selected from saccharide chains expressed by Formulas (6) and (8) respectively, the method comprising at least the step of causing a reagent to contact with GalNAc donor, GlcUA donor and a saccharide chain expressed by Formula (2), the reagent set forth in (9) or (10):

GalNAc-GlcUA-R²     (2),

(GalNAc-GlcUA)n-GalNAc-GlcUA-R²     (6),

GlcUA-(GalNAc-GlcUA)n-GalNAc-GlcUA-R²     (8), (where n is an integer not less than 1, GlcUA, GalNAc, and "-" are as defined above, R² is an arbitrary group).

(15) A probe for hybridization, the probe containing a nucleotide sequence from nucleotide numbers 495 to 2900 in SEQ. ID. NO: 1, or a sequence complementary with part of the nucleotide sequence.

BRIEF DESCRIPTION OF DRAWINGS

FIG. 1 illustrates comparison among a putative amino acid sequence of human chondroitin synthase (Human) (SEQ ID NO: 2), and amino acid sequences of homologous proteins of C. elegans (T25233) (SEQ ID NO: 5) and Drosophila (AE003499) (SEQ ID NO: 6). Those putative amino acid sequences were analyzed by using GENETYX-MAC (version 10) computer program. Respectively, the black boxes indicate that three of them have an identical amino acid, and the gray boxes indicate that two of them have an identical amino acid. The broken lines indicate gaps inserted for attaining highest degree of matching. Surrounded by the rectangular frames are predicted transmembrane domain. A DXD motif that was preserved is indicated by underline. Three sites predicted N-glycosylation sites are marked with star marks.

FIG. 3(a): A reaction product of GlcUA transferase collected from a Superdex peptide column was digested by chondroitinase AC-II or β-glucuronidase. The reaction product (black rectangle) that was not digested, the reaction product (black circle) that was digested by chondroitinase AC-II, and the reaction product that was digested by β-glucuronidase, were applied into the Superdex peptide column. Radioactivity of elution fractions of each (0.4 ml each) was analyzed. Arrows indicate elution positions of saturated disaccharide (1, GlcUAβ1-3GalNAc), or isolated GlcUA (2, [¹⁴C]GlcUA).

FIG. 3(b): A reaction product of GalNAc transferase collected from a Superdex peptide column was digested by chondroitinase AC-II. The reaction product (black rectangle) that was not digested, or the reaction product (black circle) that was digested by chondroitinase AC-II, was applied into the Superdex peptide column. Radioactivity of elution fractions of each (0.4 ml each) was analyzed. Arrows indicate elution positions of saturated disaccharide (1, GlcUAβ1-3GalNAc), or isolated GalNAc (2, [³H]GalNAc).

Figure 2:
FIG. 2 shows a genome structure of the human chondroitin synthase geneExon regions are indicated by the boxes. The black boxes indicate coding sequences, whereas the white boxes indicate 5'- and 3'-untranslated sequences. The translation initiation codon (ATG) and stop codon (TAA) are shown as well. The black horizontal line indicates introns.

Lane 7 is kidney; Lane 8 is liver; Lane 9 is small intestine; Lane 10 is placenta; Lane 11 is lung, and Lane 12 is leukocyte in peripheral blood.

BEST MODE FOR CARRYING OUT THE INVENTION

The present invention is described in detail below with reference to an embodiment of the invention.

(1) Vector of the Invention

A vector of the present invention is a vector carrying one of DNA (a), (b) or (c), excluding a DNA encoding a protein at amino-acid position #1 to 802 in SEQ. ID. NO: 2):

(a) DNA encoding a protein having an amino acid sequence from amino acid numbers 47 to 802 in SEQ. ID. NO: 2;

(b) DNA that, in a stringent condition, hybridizes with the DNA (a), the DNA complementary with DNA (a), or DNA having part of a nucleotide sequence of the DNA (a) or the DNA complementary with the DNA (a);

(c) DNA encoding a protein having an amino acid sequence from amino acid numbers 47 to 802 in SEQ. ID. NO:2, wherein one or several amino acids in the amino acid sequence are substituted, deleted, inserted, or transpositioned;

the above DNA (b) or (c) encoding a protein having catalytic activities ($\alpha$) and ($\beta$), ($\alpha$) catalytic activity that transferase GalNAc from UDP-GalNAc to chondroitin; and ($\beta$) catalytic activity that transferase GlcUA from UDP-GlcUA to chondroitin.

Note that, the foregoing chondroitin is a polymer made of repeating disaccharide units of GlcUA and GalNAc. The chondroitin includes one whose non-reducing end is GlcUA and one whose non-reducing end is GalNAc. Thus, it can be said that the transfer of GalNAc is performed with respect to chondroitin having the non-reducing end of GlcUA, and the transfer of GlcUA is performed with respect to chondroitin having the non-reducing end of GalNAc.

As it will be explained in the Examples below, it was confirmed that a protein containing the amino acid sequence from amino acid numbers 47 to 802 in SEQ. ID. NO: 2, has enzyme activity of human chondroitin synthase. It was deduced that a transmembrane domain is included in the amino-acid sequence from amino acid numbers 1 to 46 in SEQ. ID. NO: 2. In this view, use of DNA not containing a sequence for encoding the amino acid sequence from amino acid numbers 1 to 46 is preferable in that the use of such DNA enables expression of chondroitin synthase in a soluble state. More specifically, a preferable vector has "DNA encoding the amino-acid sequence from amino-acid numbers 47 to 802, the DNA containing no sequence for encoding the amino-acid sequence from amino acid numbers 1 to 46".

In naturally-existing proteins, besides polymorphism or mutation of the DNA that codes for the protein, other mutations, such as substitution, deletion, insertion, and transposition of the amino acid in its amino acid sequence may occur due to modification reaction of the created protein inside a cell or during purification. However, there has been known that some of the naturally-existing proteins in which such mutation occurs, have substantially equal physiology and biological activity to that of a protein in which such mutation has not occurred. The scope of the vector according to the present invention includes such a vector having the DNA that encodes a protein that is different slightly in terms of structure but is substantially similar in terms of function. The same is true for a case where such a mutations is introduced in the amino acid sequence of the protein artificially. In this case, it is possible to create a larger variety of mutant. For example, there has been known that a protein prepared by replacing, with serine, a cysteine residue in an amino acid sequence of human interleukin-2 (IL-2), has interleukin-2 activity (Science, 224, 1431 (1984)). Further, there has been known that a kind of protein has a peptide domain that is not essential for its activity. Examples of this peptide domain may be a signal peptide contained in an extra-cellularly secreted protein, or a pro sequence of precursor of a protease etc. Most of such domains are removed after translation or upon conversion into an activated protein. Even though these proteins have different primary structures, functions of those proteins are equivalent finally. The foregoing DNA (b) and (c) is examples of DNA encoding such proteins.

The "stringent condition" of the DNA (b) refers to a condition for forming a specific hybrid and no unspecific hybrid. (refer to Sambrook, J. et al., Molecular Cloning A Laboratory Manual, Second Edition, Cold Spring Harbor Laboratory Press (1989) etc.). The "stringent condition" may be, for example, a condition obtained by carrying out hybridization at 42° C. in a solvent containing 50% formamide, 4×SSC, 50 mM HEPES (pH7.0), 10× Denhardt's solution, and a salmon sperm DNA of 100 μg/ml, and then washing at room temperature with 2×SSC and a 0.1% SDS solution, and sequentially washing at 50° C. with 0.1×SSC and a 0.1% SDS solution.

The "several number of amino acids" of (c) refers to an acceptable number of amino acids in which such mutation that does not cause catalytic activities ($\alpha$) and ($\beta$) occurs. The catalytic activities ($\alpha$) and ($\beta$) are explained later. For example, for a protein made of 800 amino-acid residue, the acceptable number is in a range of 4 to 40, preferably 4 to 20, more preferably 4 to 10.

Note that, DNA to be carried by the vector of the present invention may have various nucleotide sequences due to degeneracy of genetic code. This is however easily understood by a person skilled in the art.

The catalytic activities ($\alpha$) and ($\beta$) can be measured by a general assay method for glycosyltransferase.

More specifically, as explained in the Examples below, the catalytic activity ($\alpha$) can be measured by a method using transfer reaction of GalNAc into chondroitin by using a UDP N-acetylgalactosamine (UDPGalNAc) as a donor, whereas the catalytic activity ($\beta$) can be measured by a method using transfer reaction of GlcUA into chondroitin by using a UDP-glucuronic acid (UDP-GlcUA) as a donor. Accordingly, by checking the presence of the transfer activities as an index, it is easy for a person skilled in the art to select at least one of substitution, deletion, insertion, and transposition of one or some of amino acid residues, the substitution, deletion, insertion, and transposition causing no substantial deterioration in the activity. Further, it is also possible to easily select DNA that codes for a protein having catalytic activities of ($\alpha$) and ($\beta$), from among DNA that hybridize under the "stringent condition".

Note that chondroitin for use herein includes both (i) one whose non-reducing terminal is GlcUA, and (ii) one whose non-reducing terminal is GalNAc.

Moreover, the protein that the DNA (b) or the DNA (c) codes for, further has the all of the following characteristics in ($\gamma$), preferably.

($\gamma$) The following acceptors substantially receive no monosaccharide from the following donors (in the bracket).

Gal$\beta$1-3Gal$\beta$1-4Xyl (UDP-GlcUA)

GlcUA$\beta$1-3Gal$\beta$1-3Gal$\beta$1-4Xyl$\beta$1-O-Ser (UDP-GalNAc)

α-thrombomodulin (UDP-GalNAc)
sheep submandubular asialomucin (UDP-Gal)
GlcNAcβ1-3Galβ1-4GlcNAcβ1-3Galβ1-4GlcNAc
(UDP-Gal)

Note that, the α-thrombomodulin includes tetrasaccharide made of GlcUAβ1-3Galβ1-3Galβ1-4Xyl. Further, the sheep submandubular asialomucin contains GalNAcα1-O-Ser/Thr.

Note that, in the foregoing condition, Gal denotes a galactose residue, Xyl denotes a xylose residue, Ser denotes a serin residue, and Thr denotes a threonine residue, respectively. The remaining symbols are all the same as above.

It is preferable that a protein that is coded for by the DNA carried by the vector of the present invention is a water-soluble protein. This is because the water-soluble protein generally does not have a transmembrane domain, and the water-soluble protein expressed is soluble to an aqueous solvent etc., thus being easy to be purified.

The DNA carried by the vector of the present invention preferably does not contain DNA encoding the amino-acid sequence from amino-acid numbers 1 to 46 in the SEQ. ID. NO: 2. Most preferable encodes finding from nucleotide numbers 633 to 2900 in the SEQ. ID. NO: 1.

Further, it is further preferable that this vector is an expression vector, since it is desirably used in the producing method of chondroitin synthase. The method will be described later.

For example, an expression vector having DNA encoding the amino-acid sequence from amino-acid numbers 47 to 802 (DNA not containing the amino-acid sequence from amino-acid numbers 1 to 46) may be prepared with the following method.

<A> Preparation of DNA Combined with the Vector

First, obtained is a cDNA clone (GenBank accession number AB023207) specified as "KIAA0990" in the HUGE protein database. Then, by using the cDNA clone as a template, amplification is carried out through PCR method with a 5'-primer (5'-CCCTCGAGGGGCTGCCGGTCCGGGC-3' (SEQ. ID. NO: 3)) containing a XhoI site, and 3'-primer (5'-CCCTCGAGCAATCTTAAAGGAGTCCTATGTA-3' (SEQ. ID. NO:4)) containing a XhoI site 138 bp downstream from the stop codon.

The PCR method may be carried out with Pfu polymerase (Stratagene, La Jolla, Calif., USA) for 34 cycles of 94° C. for 30 seconds, 55° C. for 30 seconds, and 72° C. for 180 seconds in 5% (v/v) dimethylsulfoxide. However, the PCR method may also be carried out in a general manner <B> Introduction of DNA Fragment into Vector The vector of the present invention may be prepared by introducing, into a well-known vector, the DNA obtained in the foregoing manner.

The vector into which the DNA is introduced may be selected from appropriate expression vectors (a phage vector, a plasmid vector, or the like), which enable expression of the introduced DNA. The vector should enable expression of the foregoing DNA inside the host cells into which the vector of the present invention is transfected. Such a host-vector system may be a combination of a mammalian cell such as a COS cell or 3LL-HK46 cell, with an expression vector for mammalian cells such as pGIR201 (Kitagawa, H., and Paulson, J. C. (1994) J. Biol. Chem. 269, 1394-1401), pEF-BOS (Mizushima, S., and Nagata, S. (1990) Nucleic Acid Res. 18, 5322), pCXN2 (Niwa, H., Yamanura, K. and Miyazaki, J. (1991) Gene 108, 193-200), pCMV-2 (EastmanKodak), pCEV18, pME18S (Maruyama et al. Med. Immunol., 20, 27 (1990)) or pSVL (Pharmacia Biotec); otherwise, a combination of a coliform (*E. Coli*) with en expression vector for prokaryotic cells, such as pTrcHis (produced by Inbitrogen Co., Ltd.), pGEX (produced by Pharmacia Biotec Inc.), pTrc99 (produced by Pharmacia Biotec Inc.), pKK233-3 (produced by Pharmacia Biotec Inc.), pEZZZ18 (produced by Pharmacia Biotec Inc.), pCH110 (produced by Pharmacia Biotec Inc.), pET (produced by Stratagene Co.), pBAD (produced by Inbitrogen Co., Ltd.), pRSET (produced by Inbitrogen Co., Ltd.), or pSE420 (produced by Inbitrogen Co., Ltd.). In addition, the host cell may be insect cells, yeast, or grass *bacillus*, which are used with various corresponding vectors. Among these, the combination of a mammal cell and pEF-BOS is most preferable.

Further, the vector to introduce the DNA therein may be a vector constructed to cause expression of a fusion protein made of the protein coded by the DNA and a marker peptide. This type of vector is particularly preferable in the case of purifying chondroitin synthase, which is expressed by the vector of the present invention. The marker peptide may be a protein A sequence, an insulin signal sequence, His, FLAG, CBP (calmodulin binding protein), or GST (glutathione S-transferase), for example. Fusing of such a marker peptide to a protein A sequence allows easy affinity purification, and fusing the marker peptide into an insulin signal sequence allows extra cellular secretion (into culture medium etc.) of enzyme.

In the case of any vectors, the processing may be carried out in a general way so as to allow binding of the DNA and the vector; for example, the DNA and the vector may be bonded together after treating with a restriction endonuclease or the like, and if necessary, blunting or binding of the sticky end.

More specifically, the DNA (PCR fragment) obtained through the foregoing method <A> is digested by XhoI, and the both ends of the fragment are partially filled with Klenow fragment (New England Biolabs, Beverly, Mass.), dCTP, and dTTP. Further, the pGIR201protA (J. Biol. Chem., 269, 1394-1401 (1994)) vector digested by BamHI is also partially filled with dATP and dGTP. The fragments thus obtained were then subcloned into the pGIR201protA, resulting in the fusion of the DNA encoded by the DNA created through the method <A> with the insulin signal sequence and the protein A sequence present in the vector. An NheI fragment containing this fusion protein sequence was inserted into the XbaI site of the expression vector pEF-BOS (Nucleic Acid Res., 18, 5322 (1990)), thereby obtaining an expression vector for expression of chondroitin synthase that is fused with an insulin signal sequence and a protein A sequence.

(2) Transformant of the Present Invention

A transformant of the present invention is a transformant where a host is transformed by the vector of the present invention (including a vector containing DNA encoding a protein of amino acid sequence from amino acid numbers 1 to 802 in SEQ ID NO. 2).

As used herein, "host" may be of any kind, provided that it can be recombined by a vector of the present invention. Preferably, the host is the one which can make full use of the capabilities of DNA carried by a vector of the present invention or a recombinant vector into which the same DNA is recombined. Examples of the host include: animal cells; plant cells; and microorganism cells (fungus body), and COS cell (including COS-1 cell and COS-7 cell); and more specifically, a mammalian cell including 3LL-HK 46 cell; a coliform (*E. coli*); insect cell; yeast; and grass *bacillus* are included, for example. The host can be selected as appropriate in accordance with the vector of the present invention. However, in the case where the vector for use in the present invention is a vector based on pEF-BOS, for example, a cell derived from a mammal is preferably selected, and a COS cell is more preferably selected among them.

Transformation of the host by a vector of the pre-sent invention can be performed by standard methods known in the art. For example, transformation can be performed by introducing the vector into the host by (i) a method using a reagent for transfection, (ii) DEAE-dextran method, (iii) electroporation method, or (iv) other methods.

The transformant of the present invention obtained in such a manner can be used in applications such as production of chondroitin synthase, as described later.

(3) Method of Producing Chondroitin Synthase

The method of producing chondroitin synthase of the present invention is characterized in that a transformant of the present invention is grown to obtain chondroitin synthase from the grown transformant.

As used herein, "growth" refers to a concept including proliferation of a cell as a transformant of the present invention and of a microorganism itself and growth of a creature including animal and insect into which a cell as a transformant of the present invention is introduced. Further, as used herein, "growth product" refers to a concept including a culture medium after the growth of the transformant of the present invention (supernatant of a culture solution), a cultured host cell, a secretion, and an ejection.

Conditions of the growth (culture medium, culture condition, and others) are selected as appropriate in accordance with a host to be used.

According to this production method, chondroitin synthase in various forms can be produced in accordance with a transformant to be used.

A soluble chondroitin synthase is produced by, for example, growing a transformant prepared by transformation by the expression vector having DNA encoding the amino acid sequence from amino acid numbers 47 to 802 in SEQ ID No. 2, as a vector of the present invention.

Further, an insoluble (membrane-binding) chondroitin synthase is produced by growing a transformant prepared by transformation by the expression vector having DNA encoding the amino acid sequence from amino acid numbers 1 to 802 in SEQ ID No. 2, as a vector of the present invention.

Still further, chondroitin synthase fused with a marker peptide is produced by growing a transformant prepared by transformation by an expression vector constructed so as to express a fusion protein fused with a marker peptide.

Chondroitin synthase can be obtained from the growth product by a well-known method for protein extraction and purification, depending on a form of the produced chondroitin synthase.

For example, when chondroitin synthase is produced in a soluble form secreted in a culture medium (supernatant of a culture solution), the obtained culture medium may be directly used as chondroitin synthase. Further, when chondroitin synthase is produced in a soluble form secreted in a cytoplasm or in an insoluble (membrane-bound) form, extraction of chondroitin synthase can be performed by anyone or combination of a method using a nitrogen cavitation apparatus, homogenization, glass beads mill method, sonication, osmotic shock, extraction by cell homogenization using a method such as freezing and thawing method, and surface-active agent extraction. Alternatively, the extracted product may be directly used as chondroitin synthase.

It is also possible and preferable to further purify chondroitin synthase from such culture medium and extracted product. Purification may be incomplete purification (partial purification) or complete purification, which may be selected as appropriate in accordance with (i) the intended use of chondroitin synthase, and (ii) the like.

Specifically, examples of purifying method include: any one or combination of salting-out by ammonium sulphate, sodium sulphate, or the like; centrifugal separation; dialysis; ultrafiltration; adsorption chromatography; on-exchange chromatography; hydrophobic chromatography; reverse phase chromatography; gel filtration; gel permeation chromatography; affinity chromatography; and electrophoretic migration.

For example, when chondroitin synthase is fused with protein A to produce a fusion protein, chondroitin synthase may be purified simply by affinity chromatography using a solid phase combined with IgG. Similarly, when chondroitin synthase is fused with His to produce a fusion protein, chondroitin synthase may be purified using a solid phase combined with magnetic nickel. When chondroitin synthase is fused with FLAG to produce a fusion protein, chondroitin synthase may be purified using a solid phase combined with anti-FLAG antibody. Still further, fusion with insulin signal eliminates the need for extracting operation such as cell disruption.

Production of the purified chondroitin synthase can be confirmed by analyzing its amino acid sequence, property, substrate specificity, and others.

(4) Reagent of the Present Invention

A reagent of the present invention is a chondroitin-synthesizing reagent, an enzyme protein having an amino acid sequence of ($\alpha$) or ($\beta$), the enzyme protein having catalytic activities of (I) and (II):

(A) an amino acid sequence from amino acid numbers 47 to 802 in SEQ. ID. NO: 2;

(B) the amino acid sequence of (A) in which one or more amino acid is substituted, deleted, inserted, or transferred;

($\alpha$) catalytic activity that transferase GalNAc from UDP-GalNAc to chondroitin; and ($\beta$) catalytic activity that transferase GlcUA from UDP-GlcUA to chondroitin.

The amino acid sequences of (A) and (B) are amino acid sequences respectively encoded by the DNA of (a) and (c), which are described in connection with the vector of the present invention. The amino acid sequences respectively encoded by the DNA of (a) and (c) are already described. ($\alpha$) and ($\beta$) are already described in connection with the vector of the present invention.

An enzyme protein of the present invention is not limited to the enzyme protein from amino acid numbers 47 to 802 in SEQ. ID. NO: 2. The enzyme protein of the present invention may be, for example, an enzyme protein from amino acid numbers 1 to 802 in SEQ. ID. NO: 2.

The reagent of the present invention is a chondroitin-synthesizing reagent, which makes use of effects of an enzyme protein (chondroitin synthase) including an amino acid sequence of (A) or (B). The effects are an effect of transferring GalNAc, and an effect of transferring GlcUA.

The reagent of the present invention is used in order to synthesize chondroitin. In the present specification, to "synthesize chondroitin" is a concept that covers extending a saccharide chain of chondroitin by transferring and/or adding a saccharide to the chondroitin.

The reagent of the present invention is not limited to that of a particular form. The reagent of the present invention may be in a solution form, a frozen form, or a freeze-dried form. As long as the activities of the chondroitin synthase are not influenced, another component (e.g. a support acceptable as a reagent, or the like) may be included.

(5) Method of Producing Saccharide Chain

All methods of producing a saccharide chain according to the present invention, which use a reagent of the present invention, can be categorized into the following four types in accordance with substrates of saccharide donor and receptor used.

<1> Method of producing a saccharide chain expressed by the following formula (3), including at least the step of bringing a reagent of the present invention into contact with GalNAc donor and a saccharide chain expressed by the following formula (1)

GlcUA-GalNAc-R¹ (1)

GalNAc-GlcUA-GalNAc-R¹ (3)

<2> Method of producing a saccharide chain expressed by the following formula (4), including at least the step of bringing a reagent of the present invention into contact with GlcUA donor and a saccharide chain expressed by the following formula (2)

GalNAc-GlcUA-R² (2)

GlcUA-GalNAc-GlcUA-R² (4)

<3> Method of producing a saccharide chain selected from the following formulas (5) and (7), including at least the step of bringing a reagent of the present invention into contact with GalNAc donor, GlcUA donor, and a saccharide chain expressed by the following formula (1)

GlcUA-GalNAc-R¹ (1)

(GlcUA-GalNAc)n-GlcUA-GalNAc-R¹ (5)

GalNAc-(GlcUA-GalNAc)n-GlcUA-GalNAc-R¹ (7)

<4> Method of producing a saccharide chain selected from the following formulas (6) and (8), including at least the step of bringing a reagent of the present invention into contact with GalNAc donor, GlcUA donor, and a saccharide chain expressed by the following formula (2)

GalNAc-GlcUA-R² (2)

(GalNAc-GlcUA)n-GalNAc-GlcUA-R² (6)

GlcUA-(GalNAc-GlcUA)n-GalNAc-GlcUA-R² (8)

As GlcUA donor, nucleotide hypophosphoric acid-GalNAc is preferable, and UDP-GalNAc is especially preferable.

As GlcUA donor, nucleotide hypophosphoric acid-GlcUA is preferable, and UDP-GlcUA is especially preferable.

The way of contacting is not especially limited provided that respective molecules of the chondroitin synthase, donor, and receptor (saccharide chain) are brought into contact with one another to generate enzyme reaction, the chondroitin synthase, donor, and receptor being included in a reagent of the present invention. For example, these three types of molecules may bring into contact with one another in a solution in which they are dissolved. For continuous enzyme reactions, chondroitin synthase can be used in the form of immobilized enzyme coupled with a suitable solid phase (beads, etc.), and a membrane-type reactor using a membrane such as ultrafilter membrane and dialysis membrane may be used. As in the method described in WO 00/27437, enzyme reaction can be generated by coupling a receptor with a solid phase. Still further, a bioreactor for reproducing (synthesizing) a donor may be used together.

In the above <3> and <4>, GalNAc donor and GlcUA donor do not always need to be simultaneously brought into contact with a reagent of the present invention and the saccharide chain shown by the formula (1) or (2), and these donors may be alternately brought into contact with a reagent of the present invention and the saccharide chain shown by the formula (1) or (2).

Although conditions for enzyme reaction are not limited provided that chondroitin synthase acts, enzyme reaction at about neutral pH is preferable, and enzyme reaction in a buffer having buffer action at about neutral pH is more preferable. Further, although a temperature during enzyme reaction is not especially limited provided that activity of chondroitin synthase is held, about 30 to 40° C. (e.g. 37° C.) is exemplified. When there is a substance for increasing activity of chondroitin synthase, that substance may be added. For example, it is preferable that $Mn^{2+}$ or other substance exists together. A reaction time can be determined as appropriate by a person skilled in the art in accordance with a reagent used of the present invention, the amount of donors and receptors, and other reaction conditions. Isolation of choidroitin from a reaction product, and the like process can be performed by the well known method.

Chondroitin sulfate can be produced by using a reagent of the present invention (chondroitin synthase) together with sulfotransferase.

For example, in the above method of producing a saccharide chain (method of producing chondroitin), it is possible to produce chondroitin sulfate by causing sulfate donor (3'-phosphoadenosine 5'-phosphosulfate (PAPS), or the like) to exist together with sulfotransferase to simultaneously perform generation of chondroitin and transfer of sulfuric acid. In the same manner as described above, sulfotransferase may be used as immobilized enzyme combined with a suitable solid phase (beads, etc.), and a membrane-type reactor using a membrane such as ultrafilter membrane, and dialysis membrane may be used for continuous reactions. At this moment, a bioreactor for reproducing (synthesizing) a sulfate donor may be used together.

Also, chondroitin can be produced by directly generating chondroitin in a host transformed by a vector of the present invention (transformant of the present invention).

Further, chondroitin sulfate can be directly produced in a host by introducing a vector of the present invention and cDNA encoding sulfotransferase into a host, and causing chondroitin synthase and sulfotransferase to simultaneously express in the host (transformant of the present invention including cDNA encoding sulfotransferase).

Sulfotransferase (or cDNA encoding sulfotransferase) used herein may be an enzyme that transferase sulfuric acid to chondroitin (or cDNA encoding sulfotransferase) and can be selected as appropriate from the well known enzymes in accordance with the type of a desired sulfuric acid.

Further, two or more types of sulfotransferases each having a different transfer position of sulfuric acid (or cDNAs encoding the sulfotransferases) may be used together.

As an example of sulfotransferase, chondroitin 6-O-sulfotransferase (J. Biol. Chem., 275(28), 21075-21080 (2000)) can be given, but the present invention is not limited to this, and other enzyme can be also used.

(6) Probe of the Present Invention

A probe of the present invention is a probe for hybridization having a nucleotide sequence from nucleotide numbers 495 to 2900, more preferably 633 to 2900, in SEQ ID No: 1, or having a complementary sequence partially in the same nucleotide sequence.

A probe of the present invention can be obtained by generating oligonucleotide having a nucleotide sequence from nucleotide numbers 495 to 2900, more preferably 633 to 2900, in SEQ ID No: 1, or having a complementary sequence partially in the same nucleotide sequence and labeling this oligonucleotide with a marker suitable for hybridization (e.g. radio isotope).

The length of oligonucleotide is selected as appropriate depending on conditions of hybridization using a probe of the present invention.

A probe of the present invention is expected to be a useful tool for examining biological functions of chondroitin sulfate. This is because chondroitin sulfate widely expresses and plays an important role in many tissues, especially in a brain. This probe is considered to be useful for assessment of a connection between gene and disease.

EXAMPLES

The present invention is more specifically described below with reference to examples.

Example 1

(1) In Silico Cloning of Novel Human Glycosyltransferase cDNA

Screening of HUGE protein database at Kazusa DNA Research Institute (in Chiba Prefecture; http://www.kazusa.or.jp/huge/) was conducted by the keywords "one transmembrane domain" and "galactosyltransferase family". As a result of this, one clone (KIAA0990; GenBank™ accession number AB023207) was identified. An analysis of a nucleotide sequence of this clone revealed that this clone includes (i) a 5'-untranslated region of 494 bp, (ii) a single open reading frame of 2406 bp coding for a protein of 802 amino acids with three potential N-glycosylation sites (marked with asterisks in FIG. 1), and (iii) a 3'-untranslated region of about 1.7 kb with a presumptive polyadenylation signal. The nucleotide sequence and an amino acid sequence deduced from the same are shown in SEQ. ID. NO: 1, whereas only the amino acid sequence is shown in SEQ. ID. NO: 2.

The clone was acquired from Kazusa DNA Research Institute. Northern blot analysis showed that the mRNA corresponding to the clone was about 5.0 kb in length in various human tissues (see Example 2), suggesting that the cDNA was approximately full-length. The deduced amino acid sequence corresponded to a 91,728-Da polypeptide. A predicted translation initiation site conformed to the Kozak consensus sequence for initiation (Nucleic Acids Res. 12, 857-872 (1984)), and an in-frame stop codon existed upstream of an initiation ATG codon allocated thereto.

A Kyte-Doolittle hydropathy analysis (J. Mol. Biol. 157, 105-132 (1982)) revealed one prominent hydrophobic segment of 17 amino acid residues in the $NH_2$-terminal region, predicting that the protein has a type II transmembrane topology which is typical in many Golgi localized glycosyltransferases having been cloned until today (see FIG. 1).

Database searches revealed that the amino acid sequence was, at its amino terminal, slightly homologous to human core 1 UDP-Gal:GalNAcα-Rβ1,3-Gal transferase (GenBank™ accession number AF155582), while the amino acid sequence was, at the carboxyl terminal, slightly homologous to a human UDP-Gal:GlCNAcβ-Rβ1,4-Gal transferase II (GenBank™ accession number AB024434). Glycosyltransferases being homologous to the amino acid are characterized in that the connection patterns of saccharide chains are often preserved, even though different members are specific to different donors or receptors (Biochim. Biophys. Acta 1254, 35-53 (1999)).

Thus, the features of the amino acid sequence to be encoded suggested a possibility that the identified gene product could have activities of both the β1,3-GlcUA transferase (GlcAT-II) and β1,4-GalNAc transferase (GalNAcT-II). Furthermore, a homologue of the identified human gene was found in the *Caenorhabditis elegans* genome or *Drosophila* genome. FIG. 1 illustrates that to what extent the protein sequences respectively derived from human, *C. elegans*, and *Drosophila* are homologous to each other. The human protein sequence shares 36 homologies with the sequence of the *C. elegans*, and 42 homologies with the sequence of the *Drosophila*. These three proteins all include DDD at the amino terminal and DVD at the carboxyl terminal (cf. FIG. 1), thereby being considered as a conserved DXD motif which is found in most glycosyltransferases (Proc. Natl. Acad. Sci. U.S.A. 95, 7945-7950 (199.8)).

In addition to the above, a data base search of the Human Genome Project identified agenome sequence (accession number NT010274.3) identical with the above-mentioned cDNA sequence. Comparison of the cDNA and genome sequences revealed the genomic structure and chromosomal localization of the gene. The gene spans over 40 kb, and the coding region thereof was divided into three discrete exons as shown in FIG. 2. The intron/exon junctions followed the GT/AG rule and were flanked by conserved sequences. This gene is located on the human chromosome number 15.

(2) Construction of a Plasmid Including DNA Encoding a Novel Soluble Glycosyltransferase A cDNA of a Glycosyltransferase that lacked 46 amino acid residues at its N-terminal from this novel glycosyltransferase was amplified by PCR. Specifically, with a KIAA0990 cDNA as a template, amplification was carried out using (a) a 5'-primer (5'-CCCTCGAGGGGCTGCCGGTCCGGGC-3' (SEQ. ID. NO: 3)) including an XhoI site and (b) a 3'-primer (5'-CCCTCGAGCAATCTTAAAGGAGTCCTATGTA-3' (SEQ. ID. NO: 4)) including a XhoI site located 138 bp downstream from the stop codon. The PCR was carried out with Pfu polymerase (Stratagene Co., La Jolla, Calif.) for 34 cycles of 94° C. for 30 seconds, 55° C. for 30 seconds, and 72° C. for 180 seconds in 5 (v/v) dimethyl sulfoxide. The PCR-product was then digested with the XhoI. Then, at both terminals of its fragment, the PCP product was partially filled with Klenow Fragment (New England Biolabs Inc., Beverly, Mass.), a dCTP, and a dTTP. A pGIR201protA (J. Biol. Chem. 269, 1394-1401 (1994)) vector digested with BamHI was also partially filled with a dATP and a dGTP. The obtained fragment was subcloned into the pGIR201protA, so that the novel glycosyltransferase was fused with the insulin signal sequence and the protein A sequence which were carried in the vector. An NheI fragment including the above-mentioned fusion protein sequence was inserted into the XbaI site of the expression vector pEF-BOS (Nucleic Acids Res. 18, 5322 (1990)), whereby an expression plasmid was obtained.

This expression plasmid encodes a protein in which the first 46 amino acids of the glycosyltransferase is replaced with a cleavable insulin signal sequence and a protein A IgG-binding domain. In other words, the expression plasmid encodes a soluble chondroitin synthase fused with a cleavable insulin signal sequence and a protein A.

(3) Expression of a Novel Soluble Glycosyltransferase, and Enzymatic Assay Thereof.

By using FuGENE (Trademark) 6 (Roche Molecular Biochemicals Co., Tokyo), an expression plasmid (6.7 μg) was transfected into a COS-1 cell on a 100 mm plate, in accordance with a manual of the manufacture. On the second day from the transfection, 1 ml of an incubation liquid was collected and incubated together with 10 μL of IgG-Sepharose (Amersham Pharmacia Biotech) at 4° C. for one hour. Beads of the IgG-Sepharose was collected by centrifugation, and then washed with an assay buffer. After that, the beads were resuspended in an assay buffer of the same kind as the assay buffer. The beads were used for assaying GalNAc transferase, GlcUA transferase, and Gal transferase. That is, a fused protein occurred in the incubation liquid was absorbed by IgG-Sepharose so as to remove glycosyltransferases in the incubation liquid. Then, by using the enzyme bound beads as an enzyme source, glycosyltransferase activity of the fused protein that was bound to the beads was assayed with various receptor substrates and donor substrates.

As a receptor for GalNAc transferase, a polymer (167 μg) of chondroitin, α-thrombomodulin (1 nmol), or GlcUAβ1-3Galβ1-3Galβ1-4Xylβ1-0-Ser (1 nmol) was used. Moreover, as a receptor for GlcUA transferase, the polymer (167 μg) of chondroitin or Galβ1-3Galβ1-4Xylβ (1 nmol) was used. As a receptor of Gal transferase, sheep submandibular asialomucin (300 μg) or GlcNAcβ1-3Galβ1-4GlcNAcβ1-3Galβ1-4GlcNAc (1 nmol) was used. Assay of GalNAc transferase was carried out with a mixture of, in 30 μL in total, 10 μL of the resuspended beads, the receptor substrate, 8.57 μM UDP-[$^3$H]GalNAc (3.60×10$^5$ dpm), 50 mM MES buffer, pH 6.5, 10 mM MnCl2, and 171 μM of sodium salt of ATP (J. Biochem. 117, 1083-1087 (1995)).

Assay of GlcUA transferase I (GlcAT-I), which is necessary for synthesis of tetrasaccharide for the linkage region, was carried out with a mixture of, in 30 μL in total, 10 μL of the resuspended beads, 1 nmol Galβ1-3Galβ1-4Xyl, 14.3 μM UDP-[$^{14}$C]GlcUA (1.46×10$^5$ dpm), 50 mM MES buffer, pH6.5, and 2 mM MnCl$_2$ (FEBS lett. 459, 415-420 (1999)). In assay of GlcAT-II, 10 μL of the resuspended beads, 167 μg of the polymer of chondroitin, 14.3 μM UDP-[$^{14}$C]GlcUA (1.46×10$^5$ dpm), 50 mM sodium acetic acid buffer, pH 5.6, and 10 mM MnCl2 were included in 30 μL in total (Glycobiology 7, 905-911 (1997)). Assay of Gal transferase was carried out with a mixture of, in 30 μL in total, 10 μL of the resuspended beads, the receptor substrate, 60 μM UDP-[$^3$H]Gal (5.30×10$^5$ dpm), 50 mM MES buffer, pH 6.5, 10 mM MnCl$_2$, and 171 μM of sodium salt of ATP. Reaction mixtures were incubated at 37° C. for one hour. Products that had been radiolabeled was separated from UDP-[$^3$H]GalNAc, UDP-[$^{14}$C]GlcUA, or UDP-[$^3$H]Gal, by gel filtration using a syringe column packed with Sephadex G-25 (super fine), a superdex peptide column, or a Pasteur pipette column containing Dowex 1-X8 (PO42-type, 100-400 mesh, Bio-Rad Laboratories, Tokyo) (J. Biochem. 117, 1083-1087 (1995); J. Biol. Chem. 273, 6615-6618 (1998); FEBS Lett. 459, 415-420 (1999); Glycobiology 7, 905-911 (1997); Glycobiology 7, 531-537 (1997)). The thus collected labeled products were quantified by liquid scintillation spectroscopy.

Note that the substrates and the like were obtained as follows. UDP-[U-$^{14}$C]GlcUA (285.2 mCi/mmol), UDP-[$^3$H]GalNAc (10 Ci/mmol) and UDP-[$^3$H]Gal (15 Ci/mmol) were purchased from NEN Life Science Products Inc. Unlabeled UDP-GlcUA, UDP-GalNAc and UDP-Gal were obtained from Sigma. Chondroitin (a derivative prepared by chemically desulfurizing chondroitin sulfuric acid A derived from whale cartilage) was purchased from Sekikagaku Corp. (Tokyo). Homogeneity purified Hepatopancreas β-glucuronidase (EC3.2.1.31) (Comp. Biochem. Physiol. 86B, 565-569 (1987)) derived from Amlullaria (freshwater apple snail) was provided from Tokyo Internal Organ Co. Ltd. (Tokyo).

Galβ1-3Galβ1-4Xyl was kindly provided from Dr. Nancy B. Schwartz (University of Chicago). The purified α-thrombomodulin (Biochem. Biophys. Res. Coummn. 171, 729-737 (1990)) was provided from Daiichi Pharmaceutical Co. Ltd (Tokyo) and included the tetrasaccharide (GlcUAβ1-3Galβ1-3Galβ1-4Xyl) (J. Biol. Chem. 273, 33728-33734 (1998)) for the linkage region. N-acetyl chondroitin (GlcUAβ1-3GalNAc) and GlcNAcβ1-3Galβ1-4GlcNAcβ1-3Galβ1-4GlcNAc was kindly provided from Dr. K. Yoshida (Seikagaku Corp.). Linkage tetrasaccharide-serine (GlcUAβ1-3Galβ1-3Galβ1-4Xylβ1-O-Ser) (Liebigs Ann. 1239-1257 (1996)) was kindly provided from Dr. T. Ogawa (Physical and Chemical Research Institute, Saitama Prefecture).

Sheep submandibular asialomucin was obtained by treating sheep submandibular mucin with sialidase derived from *Arthrobacter ureafaciens* (Nacalai Tesque Inc. Kyoto), the sheep submandubular mucin having been prepared according to methods of Tettamanti and Pigman (Arch. Biochem. Biophys. 124, 45-50 (1968)). Superdex (Trademark) peptide HR10/30 column was supplied from Amersham Pharmacia Biotech (Uppsala, Sweden).

Results were shown in Table 1. Activities were detected when the polymer of chondroitin was used as the receptor and UDP-GLcUA or UDP-GlNAc was used as the donor. On the other hand, no activity was detected when the other receptor substrate was used and one of UDP-GlcUA, UDP-GalNAc and UDP-Gal was used as the donor. Such activities included activities of (a) GlcAT-I (which relates to initiation of biosynthesis of chondroitin sulfate), (b) GalNAc transferase I, (c) core 1 UDP-Gal:GalNAc α-R β 1,3-Gal transferase, and (d) UDP-Gal:GlcNAc β-R β 1,4-Gal transferase. Glycosyltransferase activity was not detected in an affinity purification product that was a sample prepared as a control by transfecting pEF-BOS. Those results clearly show that expressed proteins were GlcUA/GalNAc transferases having a high specificity for the polymer of chondroitin.

As described above, chondroitin (the polymer of chondroitin) includes one whose non-reducing terminal is GlcUA and one whose non-reducing terminal is GalNAc. It can be said that the transfer of GalNAc is for the chondroitin whose non-reducing terminal is GlcUA, and the transfer of GlcUA is for the chondroitin whose non-reducing terminal is GalNAc.

TABLE 1

RECEPTOR SPECIFICITY

| RECEPTOR (DONOR) | ACTIVITY 3) (pmol/ml medium/time) |
|---|---|
| Chondroitin (UDP-GlcUA) | 5.2 |
| Galβ1-3Galβ1-4Xyl (UDP-GlcUA) | ND |
| Chondroitin (UDP-GalNAc) | 1.4 |
| GlcUAβ1-3Galβ1-4Xylβ-O-Ser(UDP-GalNAc) | ND |
| α-thrombomodulin (UDP-GalNAc) | ND |
| Sheep submandubular asialomucin (UDP-Gal) | ND |
| GlcNAcβ1-3Galβ1-4GlcNAcβ1-3Galβ1-4GlcNAc(UDP-Gal) | ND |

ND: Not Detected (<0.1 pmol/ml medium/time)
1) α-thrombomodulin included tetrasaccharide linkage GlcUAβ1-3Galβ1-3Galβ1-4Xyl (J. Biol. Chem. 273, 33728-33734 (1998)).
2) Sheep submandibular asialomucin had a large number of GalNAc α 1-O-Ser/Thr residues.
3) Each value is an average of the measures taken in two independents experiments.

(4) Identification of Enzymatic Reaction Products

Isolation of products of GalNAc transferase reaction or GlcUA transferase reaction, in which the polymer of chondroitin was used as the receptor, was carried out by using gel filtration using a superdex peptide column that had been equilibrated with 0.25 m NH$_4$HCO$_3$/7-propanol. With radioactivity peak pooled, the radioactivity peak containing each enzymatic reaction was evaporated to dryness. The thus isolated products (about 120 μg) of GalNAc transferase reaction was digested, at 37° C. for one night, in a reaction liquid of 30 μL by using 100 mIU of Chondroitinase AC-II (EC4.2.2.5) (Seikagaku Corp. (Tokyo)) derived from *Arthrobacter aure-* scens, the reaction liquid containing 50 mM sodium acetic acid buffer, at pH 6.0. Degree of digestion thereof was evaluated. The thus isolated products (about 180 μg) of GlcUA transferase reaction was digested for one night at 37° C. in 30 μL of 50 mM sodium acetic acid buffer, at pH6.0, containing 100 mIU of chondroitinase AC-II, or in 30 μL of 0.05M sodium citric acid buffer, at pH4.5, containing 22mIU of β-glucuronidase. Digestion products of each enzyme were analyzed by using the same superdex peptide column.

Figure 3:
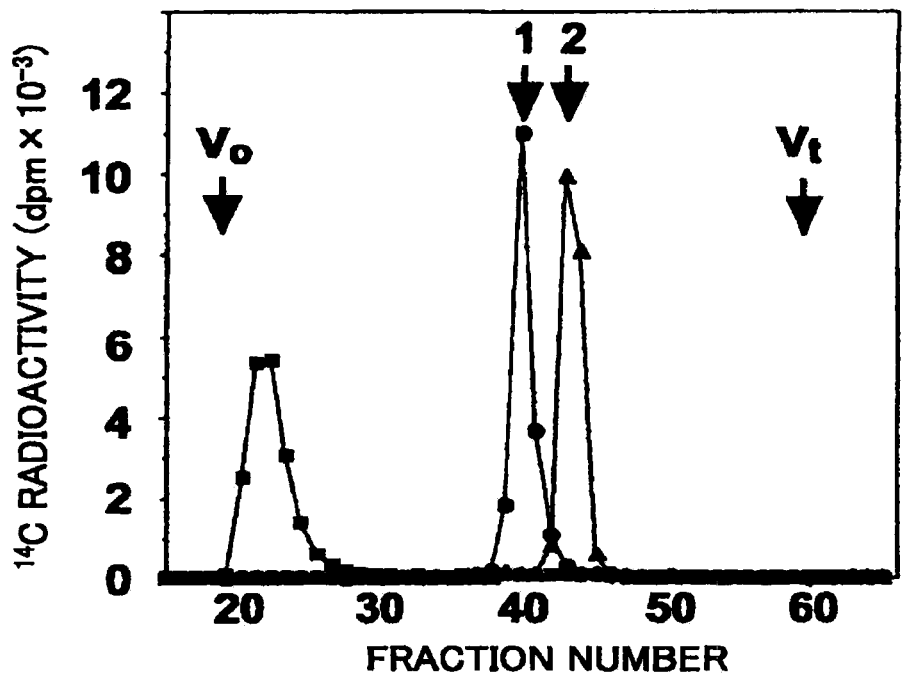
FIGS. 3(a) and 3(b) show results of identification of reaction products from human chondroitin synthase reaction.
Figure 3:
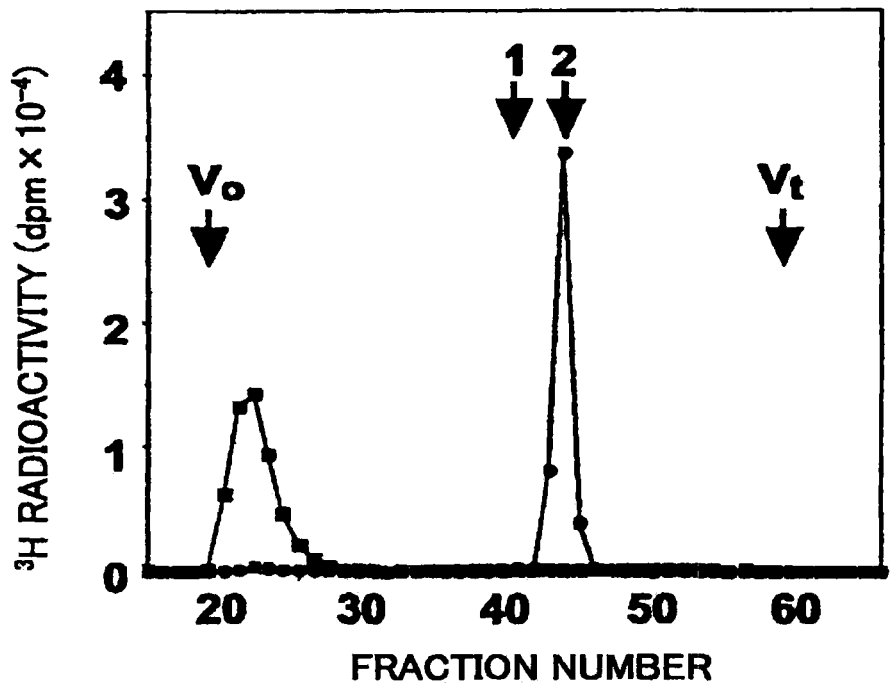

An analysis result of the products of the GlcUA transferase reaction is shown in FIG. 3(a). The labeled products were completely digested by β-glucuronidase or chondroitinase AC-II. Peaks were observed at positions of free [$^{14}$C]GlcUA or free [$^{14}$C]GlcUAβ1-3GalNAc. This result suggests that the GlcUA residue is transferred to GalNAc that existed at the non-reducing terminal of the polymer of chondroitin, and caused the GlcUA residue to form β1-3 bonding with GalNAc.

An analysis result of the products of the GalNAc transferase reaction is shown in FIG. 3(b). The labeled products were completely digested by chondroitinase AC-II. A Peak was observed at a position of free [$^3$H]GalNAc. This result suggests that the GalNAc residue is transferred to GlcUA that existed at the non-reducing terminal of the polymer of chondroitin, and caused the GalNAc residue to form β1-4 bonding with GlcUA. To sum up the results, it was found that the proteins thus identified were chondroitin synthase that had both the activities of GlcAT-II and GalNAcT-II.

Example 2

A commercially-available human 12-lane multiple tissue Northern blot (Clontech) membrane was used for analysis. To each lane, 1 μg of a polyadenylated RNA was applied. The membrane was probed with a gel-purified and radiolabeled (>1×10$^9$ cpm/μg) 0.84 kb chondroitin-synthase-specific fragment corresponding to nucleotides 631-1469 of the KIAA0990 cDNA (GenBank™ accession number AB023207).

Figure 4:
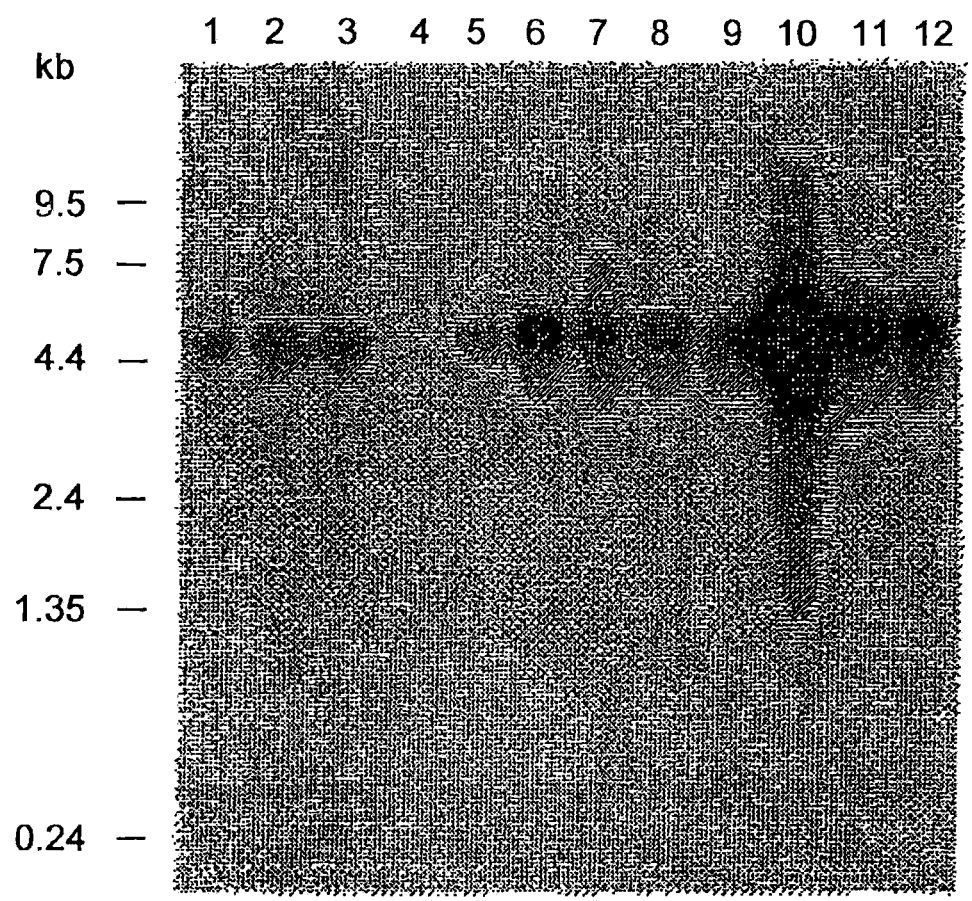
FIG. 4 shows a result of Northern blot analysis (a photograph of gel-electrophoresis) of chondroitin synthase in a human tissue. Hybridization of RNAs derived from various human tissues was carried out by using probes of chondroitin synthase: Lane 1 is brain; Lane 2 is heart; Lane 3 is skeletal muscle; Lane 4 is colon; Lane 5 is thymus; Lane 6 is spleen.

As a result, a single band of up to 5.0 kb was demonstrated for all human tissues, at least in this analysis (FIG. 4). The degree of the expression of the chondroitin synthase gene which is prevalent in human tissues varied with the types of human tissues. Notably, a particularly strong expression of the mRNA was observed in the placenta. The expressions observed in the spleen, lung, and peripheral blood leukocytes were also strong but not as much as that of the placenta. This result corresponds to an observation that chondroitin sulfate proteoglycans are distributed at the surfaces of many cells and in the extracellular matrix of almost all tissues.

Industrial Applicability

Provided are (a) a vector having DNA encoding human chondroitin synthase, (b) a method of producing human chondroitin synthase, (c) a method of producing a saccharide chain having a repeating disaccharide unit of chondroitin, and (d) a probe for hybridization of human chondroitin synthase.

The invention claimed is:

1. A method for producing a saccharide chain of Formula (4), the method comprising at least the step of causing a reagent to contact with a GlcUA donor and a saccharide chain of Formula (2):

  (2),

  (4), where GlcUA is an N-glucuronic acid residue, GalNAc is an N-acetylgalactosamine residue, "-" indicates a glycoside linkage, and $R^2$ is an arbitrary group, and the reagent has an enzyme that has an amino acid sequence including an amino acid sequence (A) or (B) and has catalytic activities ($\alpha$) and ($\beta$); wherein:

(A) is the amino acid sequence from amino acid numbers 47 to 802 in SEQ ID NO: 2;

(B) is the amino acid sequence from amino acid numbers 47 to 802 in SEQ ID NO: 2, wherein one to forty amino acids in the amino acid sequence are substituted, deleted, or inserted;

($\alpha$) is the catalytic activity that transfers GalNAc from UDP-GalNAc to chondroitin, where UDP is uridine 5' diphosphate, and GalNAc is N-acetylgalactosamine residue; and ($\beta$) is the catalytic activity that transfers GlcUA from UDP-GlcUA to chondroitin, where UDP is uridine 5' diphosphate and GlcUA is glucuronic acid residue.

2. The method as set forth in claim 1, wherein the enzyme is soluble.

* * * * *

SEQUENCE LISTING

```
<160> NUMBER OF SEQ ID NOS: 6

<210> SEQ ID NO 1
<211> LENGTH: 4565
<212> TYPE: DNA
<213> ORGANISM: Homo sapiens
<220> FEATURE:
<221> NAME/KEY: CDS
<222> LOCATION: (495)..(2900)

<400> SEQUENCE: 1
ggcgagctaa  gccggaggat  gtgcagctgc  ggcggcggcg  ccggctacga  agaggacggg         60
gacaggcgcc  gtgcgaaccg  agcccagcca  gccggaggac  gcgggcaggg  cgggacggga        120
gcccggactc  gtctgccgcc  gccgtcgtcg  ccgtcgtgcc  ggccccgcgt  ccccgcgcgc        180
gagcgggagg  agccgccgcc  acctcgcgcc  cgagccgccg  ctagcgcgcg  ccgggcatgg        240
tcccctctta  aaggcgcagg  ccgcggcggc  ggggcgggc  gtgcggaaca  aagcgccggc        300
gcggggcctg  cgggcggctc  ggggccgcg  atgggcgcgg  cgggcccgcg  gcggcggcgg        360
cgctgcccgg  gccgggcctc  gcggcgctag  ggcgggctgg  cctccgcggg  cggggcagc        420 gggctgaggg  cgcgcggggc  ctgcggcggc  ggcggcgcg  cggcggcgg  cccggcgggc        480 ggagcggcgc  gggc atg gcc gcg cgc ggc cgg cgc gcc tgg ctc agc gtg            530
        Met Ala Ala Arg Gly Arg Arg Ala Trp Leu Ser Val
          1               5                  10 ctg ctc ggg ctc gtc ctg ggc ttc gtg ctg gcc tcg cgg ctc gtc ctg            578
Leu Leu Gly Leu Val Leu Gly Phe Val Leu Ala Ser Arg Leu Val Leu
         15                  20                  25 ccc cgg gct tcc gag ctg aag cga gcg ggc cca cgg cgc cgc gcc agc            626
Pro Arg Ala Ser Glu Leu Lys Arg Ala Gly Pro Arg Arg Arg Ala Ser
     30                  35                  40 ccc gag ggc tgc cgg tcc ggg cag gcg gcg gct tcc cag gcc ggc ggg            674
```

-continued

```
                Pro Glu Gly Cys Arg Ser Gly Gln Ala Ala Ser Gln Ala Gly Gly
                 45                  50                  55                  60 gcg cgc ggc gat gcg cgc ggg gcg cag ctc tgg ccg ccc ggc tcg gac      722
Ala Arg Gly Asp Ala Arg Gly Ala Gln Leu Trp Pro Pro Gly Ser Asp
                 65                  70                  75 cca gat ggc ggc ccg cgc gac agg aac ttt ctc ttc gtg gga gtc atg      770
Pro Asp Gly Gly Pro Arg Asp Arg Asn Phe Leu Phe Val Gly Val Met
             80                  85                  90 acc gcc cag aaa tac ctg cag act cgg gcc gtg gcc gcc tac aga aca      818
Thr Ala Gln Lys Tyr Leu Gln Thr Arg Ala Val Ala Ala Tyr Arg Thr
         95                 100                 105 tgg tcc aag aca att cct ggg aaa gtt cag ttc ttc tca agt gag ggt      866
Trp Ser Lys Thr Ile Pro Gly Lys Val Gln Phe Phe Ser Ser Glu Gly
    110                 115                 120 tct gac aca tct gta cca att cca gta gtg cca cta cgg ggt gtg gac      914
Ser Asp Thr Ser Val Pro Ile Pro Val Val Pro Leu Arg Gly Val Asp
125                 130                 135                 140 gac tcc tac ccg ccc cag aag aag tcc ttc atg atg ctc aag tac atg      962
Asp Ser Tyr Pro Pro Gln Lys Lys Ser Phe Met Met Leu Lys Tyr Met
                145                 150                 155 cac gac cac tac ttg gac aag tat gaa tgg ttt atg aga gca gat gat     1010
His Asp His Tyr Leu Asp Lys Tyr Glu Trp Phe Met Arg Ala Asp Asp
            160                 165                 170 gac gtg tac atc aaa gga gac cgt ctg gag aac ttc ctg agg agt ttg     1058
Asp Val Tyr Ile Lys Gly Asp Arg Leu Glu Asn Phe Leu Arg Ser Leu
        175                 180                 185 aac agc agc gag ccc ctc ttt ctt ggg cag aca ggc ctg ggc acc acg     1106
Asn Ser Ser Glu Pro Leu Phe Leu Gly Gln Thr Gly Leu Gly Thr Thr
    190                 195                 200 gaa gaa atg gga aaa ctg gcc ctg gag cct ggt gag aac ttc tgc atg     1154
Glu Glu Met Gly Lys Leu Ala Leu Glu Pro Gly Glu Asn Phe Cys Met
205                 210                 215                 220 ggg ggg cct ggc gtg atc atg agc cgg gag gtg ctt cgg aga atg gtg     1202
Gly Gly Pro Gly Val Ile Met Ser Arg Glu Val Leu Arg Arg Met Val
                225                 230                 235 ccg cac att ggc aag tgt ctc cgg gag atg tac acc acc cat gag gac     1250
Pro His Ile Gly Lys Cys Leu Arg Glu Met Tyr Thr Thr His Glu Asp
            240                 245                 250 gtg gag gtg gga agg tgt gtc cgg agg ttt gca ggg gtg cag tgt gtc     1298
Val Glu Val Gly Arg Cys Val Arg Arg Phe Ala Gly Val Gln Cys Val
        255                 260                 265 tgg tct tat gag atg cag cag ctt ttt tat gag aat tac gag cag aac     1346
Trp Ser Tyr Glu Met Gln Gln Leu Phe Tyr Glu Asn Tyr Glu Gln Asn
    270                 275                 280 aaa aag ggg tac att aga gat ctc cat aac agt aaa att cac caa gct     1394
Lys Lys Gly Tyr Ile Arg Asp Leu His Asn Ser Lys Ile His Gln Ala
285                 290                 295                 300 atc aca tta cac ccc aac aaa aac cca ccc tac cag tac agg ctc cac     1442
Ile Thr Leu His Pro Asn Lys Asn Pro Pro Tyr Gln Tyr Arg Leu His
                305                 310                 315 agc tac atg ctg agc cgc aag ata tcc gag ctc cgc cat cgc aca ata     1490
Ser Tyr Met Leu Ser Arg Lys Ile Ser Glu Leu Arg His Arg Thr Ile
            320                 325                 330 cag ctg cac cgc gaa att gtc ctg atg agc aaa tac agc aac aca gaa     1538
Gln Leu His Arg Glu Ile Val Leu Met Ser Lys Tyr Ser Asn Thr Glu
        335                 340                 345 att cat aaa gag gac ctc cag ctg gga atc cct ccc tcc ttc atg agg     1586
Ile His Lys Glu Asp Leu Gln Leu Gly Ile Pro Pro Ser Phe Met Arg
    350                 355                 360 ttt cag ccc cgc cag cga gag gag att ctg gaa tgg gag ttt ctg act     1634
Phe Gln Pro Arg Gln Arg Glu Glu Ile Leu Glu Trp Glu Phe Leu Thr
```

```
Phe Gln Pro Arg Gln Arg Glu Glu Ile Leu Glu Trp Glu Phe Leu Thr
365                 370                 375                 380 gga aaa tac ttg tat tcg gca gtt gac ggc cag ccc cct cga aga gga      1682
Gly Lys Tyr Leu Tyr Ser Ala Val Asp Gly Gln Pro Pro Arg Arg Gly
                385                 390                 395 atg gac tcc gcc cag agg gaa gcc ttg gac gac att gtc atg cag gtc      1730
Met Asp Ser Ala Gln Arg Glu Ala Leu Asp Asp Ile Val Met Gln Val
            400                 405                 410 atg gag atg atc aat gcc aac gcc aag acc aga ggg cgc atc att gac      1778
Met Glu Met Ile Asn Ala Asn Ala Lys Thr Arg Gly Arg Ile Ile Asp
        415                 420                 425 ttc aaa gag atc cag tac ggc tac cgc cgg gtg aac ccc atg tat ggg      1826
Phe Lys Glu Ile Gln Tyr Gly Tyr Arg Arg Val Asn Pro Met Tyr Gly
    430                 435                 440 gct gag tac atc ctg gac ctg ctt ctg tac aaa aag cac aaa ggg          1874
Ala Glu Tyr Ile Leu Asp Leu Leu Leu Tyr Lys Lys His Lys Gly
445                 450                 455                 460 aag aaa atg acg gtc cct gtg agg agg cac gcg tat tta cag cag act      1922
Lys Lys Met Thr Val Pro Val Arg Arg His Ala Tyr Leu Gln Gln Thr
                465                 470                 475 ttc agc aaa atc cag ttt gtg gag cat gag gag ctg gat gca caa gag      1970
Phe Ser Lys Ile Gln Phe Val Glu His Glu Glu Leu Asp Ala Gln Glu
            480                 485                 490 ttg gcc aag aga atc aat cag gaa tct gga tcc ttg tcc ttt ctc tca      2018
Leu Ala Lys Arg Ile Asn Gln Glu Ser Gly Ser Leu Ser Phe Leu Ser
        495                 500                 505 aac tcc ctg aag aag ctc gtc ccc ttt cag ctc cct ggg tcg aag agt      2066
Asn Ser Leu Lys Lys Leu Val Pro Phe Gln Leu Pro Gly Ser Lys Ser
    510                 515                 520 gag cac aaa gaa ccc aaa gat aaa aag ata aac ata ctg att cct ttg      2114
Glu His Lys Glu Pro Lys Asp Lys Lys Ile Asn Ile Leu Ile Pro Leu
525                 530                 535                 540 tct ggg cgt ttc gac atg ttt gtg aga ttt atg gga aac ttt gag aag      2162
Ser Gly Arg Phe Asp Met Phe Val Arg Phe Met Gly Asn Phe Glu Lys
                545                 550                 555 acg tgt ctt atc ccc aat cag aac gtc aag ctc gtg gtt ctg ctt ttc      2210
Thr Cys Leu Ile Pro Asn Gln Asn Val Lys Leu Val Val Leu Leu Phe
            560                 565                 570 aat tct gac tcc aac cct gac aag gcc aaa caa gtt gaa ctg atg aca      2258
Asn Ser Asp Ser Asn Pro Asp Lys Ala Lys Gln Val Glu Leu Met Thr
        575                 580                 585 gat tac cgc att aag tac cct aaa gcc gac atg cag att ttg cct gtg      2306
Asp Tyr Arg Ile Lys Tyr Pro Lys Ala Asp Met Gln Ile Leu Pro Val
    590                 595                 600 tct gga gag ttt tca aga gcc ctg gcc ctg gaa gta gga tcc tcc cag      2354
Ser Gly Glu Phe Ser Arg Ala Leu Ala Leu Glu Val Gly Ser Ser Gln
605                 610                 615                 620 ttt aac aat gaa tct ttg ctc ttc ttc tgc gac gtc gac ctc gtc ttt      2402
Phe Asn Asn Glu Ser Leu Leu Phe Phe Cys Asp Val Asp Leu Val Phe
                625                 630                 635 act aca gaa ttc ctt cag cga tgt cga gca aat aca gtt ctg ggc caa      2450
Thr Thr Glu Phe Leu Gln Arg Cys Arg Ala Asn Thr Val Leu Gly Gln
            640                 645                 650 caa ata tat ttt cca atc atc ttc agc cag tat gac cca aag att gtt      2498
Gln Ile Tyr Phe Pro Ile Ile Phe Ser Gln Tyr Asp Pro Lys Ile Val
        655                 660                 665 tat agt ggg aaa gtt ccc agt gac aac cat ttt gcc ttt act cag aaa      2546
Tyr Ser Gly Lys Val Pro Ser Asp Asn His Phe Ala Phe Thr Gln Lys
    670                 675                 680 act ggc ttc tgg aga aac tat ggg ttt ggc atc acg tgt att tat aag      2594
Thr Gly Phe Trp Arg Asn Tyr Gly Phe Gly Ile Thr Cys Ile Tyr Lys
```

```
                Thr Gly Phe Trp Arg Asn Tyr Gly Phe Gly Ile Thr Cys Ile Tyr Lys
                685                 690                 695                 700 gga gat ctt gtc cga gtg ggt ggc ttt gat gtt tcc atc caa ggc tgg        2642
Gly Asp Leu Val Arg Val Gly Gly Phe Asp Val Ser Ile Gln Gly Trp
                705                 710                 715 ggg ctg gag gat gtg gac ctt ttc aac aag gtt gtc cag gca ggt ttg        2690
Gly Leu Glu Asp Val Asp Leu Phe Asn Lys Val Val Gln Ala Gly Leu
                720                 725                 730 aag acg ttt agg agc cag gaa gta gga gta gtc cac gtc cac cat cct        2738
Lys Thr Phe Arg Ser Gln Glu Val Gly Val Val His Val His His Pro
                735                 740                 745 gtc ttt tgt gat ccc aat ctt gac ccc aaa cag tac aaa atg tgc ttg        2786
Val Phe Cys Asp Pro Asn Leu Asp Pro Lys Gln Tyr Lys Met Cys Leu
                750                 755                 760 ggg tcc aaa gca tcg acc tat ggg tcc aca cag cag ctg gct gag atg        2834
Gly Ser Lys Ala Ser Thr Tyr Gly Ser Thr Gln Gln Leu Ala Glu Met
765                 770                 775                 780 tgg ctg gaa aaa aat gat cca agt tac agt aaa agc agc aat aat aat        2882
Trp Leu Glu Lys Asn Asp Pro Ser Tyr Ser Lys Ser Ser Asn Asn Asn
                785                 790                 795 ggc tca gtg agg aca gcc taatgtccag ctttgctgga aagacgtttt              2930
Gly Ser Val Arg Thr Ala
                800 ttaattatct aatttatttt tcaaaaattt tttgtatgat cagttttttga agtccgtata    2990
caaggatata ttttacaagt ggttttctta cataggactc ctttaagatt gagctttctg    3050
aacaagaagg tgatcagtgt ttgcctttga acacatcttc ttgctgaaca ttatgtagca    3110
gacctgctta actttgactt gaaatgtacc tgatgaacaa aactttttta aaaaaatgtt    3170
ttcttttgag acccttttgct ccagtcctat ggcagaaaac gtgaacattc ctgcaaagta   3230
ttattgtaac aaaacactgt aactctggta aatgttctgt tgtgattgtt aacattccac    3290
agattctacc ttttgtgttt tgttttttt tttttacaat tgttttaaag ccatttcatg     3350
ttccagttgt aagataagga aatgtgataa tagctgtttc atcattgtct tcaggagagc    3410
tttccagagt tgatcatttc ccctcatggt actctgctca gcatggccac gtaggttttt    3470
tgtttgtttt gttttgttct ttttttgaga cggagtctca ctctgttacc caggctggaa    3530
tgcagtggcg caatcttggc tcactttaac ctccacttcc ctggttcaag caattcccct    3590
gcctttgcct cccgagtagc tgggattaca ggcacacacc accacgccca gctagttttt    3650
ttgtatttt agtagagacg gggtttcacc atgcaagccc agctggccac gtaggtttta    3710
aagcaagggg cgtgaagaag gcacagtgag gtatgtggct gttctcgtgg tagttcattc    3770
ggcctaaata gacctggcat taaatttcaa gaaggatttg gcattttctc ttcttgaccc    3830
ttctctttaa agggtaaaat attaatgttt agaatgacaa agatgaatta ttacaataaa    3890
tctgatgtac acagactgaa acacacacac atacaccccta atcaaaacgt tggggaaaaa   3950
tgtatttggt tttgttcctt tcatcctgtc tgtgttatgt gggtggagat ggttttcatt    4010
ctttcattac tgttttgttt tatccttttgt atctgaaata cctttaattt atttaatatc   4070
tgttgttcag agctctgcca tttcttgagt acctgttagt tagtattatt tatgtgtatc    4130
gggagtgtgt ttagtctgtt ttatttgcag taaaccgatc tccaaagatt tccttttgga    4190
aacgcttttt ccctcctta attttatat tccttactgt tttactaaat attaagtgtt      4250
ctttgacaat tttggtgctc atgtgttttg gggacaaaag tgaaatgaat ctgtcattat    4310
accagaaagt taaattctca gatcaaatgt gccttaataa atttgttttc atttagtttt    4370
caaacagtga tagacttgcc attttaatac acgtcattgg agggctgcgt atttgtaaat    4430
```

```
agcctgatgc tcatttggaa aaataaacca gtgaacaata ttttctatt gtacttttca    4490 gaaccatttt gtctcattat tcctgtttta gctgaagaat tgtattacat ttggagagta    4550
aaaaacttaa acacg                                                    4565
```

<210> SEQ ID NO 2
<211> LENGTH: 802
<212> TYPE: PRT
<213> ORGANISM: Homo sapiens

<400> SEQUENCE: 2

```
Met Ala Ala Arg Gly Arg Arg Ala Trp Leu Ser Val Leu Leu Gly Leu
  1               5                  10                  15

Val Leu Gly Phe Val Leu Ala Ser Arg Leu Val Leu Pro Arg Ala Ser
                 20                  25                  30

Glu Leu Lys Arg Ala Gly Pro Arg Arg Ala Ser Pro Glu Gly Cys
             35                  40                  45

Arg Ser Gly Gln Ala Ala Ser Gln Ala Gly Ala Arg Gly Asp
         50                  55                  60

Ala Arg Gly Ala Gln Leu Trp Pro Pro Gly Ser Asp Pro Asp Gly Gly
 65                  70                  75                  80

Pro Arg Asp Arg Asn Phe Leu Phe Val Gly Val Met Thr Ala Gln Lys
                 85                  90                  95

Tyr Leu Gln Thr Arg Ala Val Ala Ala Tyr Arg Thr Trp Ser Lys Thr
                100                 105                 110

Ile Pro Gly Lys Val Gln Phe Phe Ser Ser Glu Gly Ser Asp Thr Ser
            115                 120                 125

Val Pro Ile Pro Val Val Pro Leu Arg Gly Val Asp Asp Ser Tyr Pro
130                 135                 140

Pro Gln Lys Lys Ser Phe Met Met Leu Lys Tyr Met His Asp His Tyr
145                 150                 155                 160

Leu Asp Lys Tyr Glu Trp Phe Met Arg Ala Asp Asp Val Tyr Ile
                165                 170                 175

Lys Gly Asp Arg Leu Glu Asn Phe Leu Arg Ser Leu Asn Ser Ser Glu
            180                 185                 190

Pro Leu Phe Leu Gly Gln Thr Gly Leu Gly Thr Thr Glu Glu Met Gly
        195                 200                 205

Lys Leu Ala Leu Glu Pro Gly Glu Asn Phe Cys Met Gly Gly Pro Gly
    210                 215                 220

Val Ile Met Ser Arg Glu Val Leu Arg Arg Met Val Pro His Ile Gly
225                 230                 235                 240

Lys Cys Leu Arg Glu Met Tyr Thr Thr His Glu Asp Val Glu Val Gly
                245                 250                 255

Arg Cys Val Arg Arg Phe Ala Gly Val Gln Cys Val Trp Ser Tyr Glu
            260                 265                 270

Met Gln Gln Leu Phe Tyr Glu Asn Tyr Glu Gln Asn Lys Lys Gly Tyr
        275                 280                 285

Ile Arg Asp Leu His Asn Ser Lys Ile His Gln Ala Ile Thr Leu His
    290                 295                 300

Pro Asn Lys Asn Pro Pro Tyr Gln Tyr Arg Leu His Ser Tyr Met Leu
305                 310                 315                 320

Ser Arg Lys Ile Ser Glu Leu Arg His Arg Thr Ile Gln Leu His Arg
                325                 330                 335

Glu Ile Val Leu Met Ser Lys Tyr Ser Asn Thr Glu Ile His Lys Glu
            340                 345                 350
```

```
Asp Leu Gln Leu Gly Ile Pro Pro Ser Phe Met Arg Phe Gln Pro Arg
            355                 360                 365

Gln Arg Glu Glu Ile Leu Glu Trp Glu Phe Leu Thr Gly Lys Tyr Leu
        370                 375                 380

Tyr Ser Ala Val Asp Gly Gln Pro Arg Arg Gly Met Asp Ser Ala
385                 390                 395                 400

Gln Arg Glu Ala Leu Asp Asp Ile Val Met Gln Val Met Glu Met Ile
                405                 410                 415

Asn Ala Asn Ala Lys Thr Arg Gly Arg Ile Ile Asp Phe Lys Glu Ile
                420                 425                 430

Gln Tyr Gly Tyr Arg Arg Val Asn Pro Met Tyr Gly Ala Glu Tyr Ile
            435                 440                 445

Leu Asp Leu Leu Leu Tyr Lys Lys His Lys Gly Lys Lys Met Thr
        450                 455                 460

Val Pro Val Arg Arg His Ala Tyr Leu Gln Gln Thr Phe Ser Lys Ile
465                 470                 475                 480

Gln Phe Val Glu His Glu Leu Asp Ala Gln Glu Leu Ala Lys Arg
                485                 490                 495

Ile Asn Gln Glu Ser Gly Ser Leu Ser Phe Leu Ser Asn Ser Leu Lys
                500                 505                 510

Lys Leu Val Pro Phe Gln Leu Pro Gly Ser Lys Ser Glu His Lys Glu
            515                 520                 525

Pro Lys Asp Lys Lys Ile Asn Ile Leu Ile Pro Leu Ser Gly Arg Phe
        530                 535                 540

Asp Met Phe Val Arg Phe Met Gly Asn Phe Glu Lys Thr Cys Leu Ile
545                 550                 555                 560

Pro Asn Gln Asn Val Lys Leu Val Val Leu Leu Phe Asn Ser Asp Ser
                565                 570                 575

Asn Pro Asp Lys Ala Lys Gln Val Glu Leu Met Thr Asp Tyr Arg Ile
            580                 585                 590

Lys Tyr Pro Lys Ala Asp Met Gln Ile Leu Pro Val Ser Gly Glu Phe
        595                 600                 605

Ser Arg Ala Leu Ala Leu Glu Val Gly Ser Ser Gln Phe Asn Asn Glu
        610                 615                 620

Ser Leu Leu Phe Phe Cys Asp Val Asp Leu Val Phe Thr Thr Glu Phe
625                 630                 635                 640

Leu Gln Arg Cys Arg Ala Asn Thr Val Leu Gly Gln Gln Ile Tyr Phe
                645                 650                 655

Pro Ile Ile Phe Ser Gln Tyr Asp Pro Lys Ile Val Tyr Ser Gly Lys
            660                 665                 670

Val Pro Ser Asp Asn His Phe Ala Phe Thr Gln Lys Thr Gly Phe Trp
        675                 680                 685

Arg Asn Tyr Gly Phe Gly Ile Thr Cys Ile Tyr Lys Gly Asp Leu Val
        690                 695                 700

Arg Val Gly Gly Phe Asp Val Ser Ile Gln Gly Trp Gly Leu Glu Asp
705                 710                 715                 720

Val Asp Leu Phe Asn Lys Val Val Gln Ala Gly Leu Lys Thr Phe Arg
                725                 730                 735

Ser Gln Glu Val Gly Val Val His Val His Pro Val Phe Cys Asp
            740                 745                 750

Pro Asn Leu Asp Pro Lys Gln Tyr Lys Met Cys Leu Gly Ser Lys Ala
        755                 760                 765

Ser Thr Tyr Gly Ser Thr Gln Gln Leu Ala Glu Met Trp Leu Glu Lys
```

```
                770              775              780
Asn Asp Pro Ser Tyr Ser Lys Ser Ser Asn Asn Gly Ser Val Arg
785              790              795              800

Thr Ala

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccctcgaggg gctgccggtc cgggc                                              25

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccctcgagca atcttaaagg agtcctatgt a                                       31

<210> SEQ ID NO 5
<211> LENGTH: 715
<212> TYPE: PRT
<213> ORGANISM: Caenorhabditis elegans

<400> SEQUENCE: 5

Met Arg Val Arg Ser Thr Cys Arg Met Pro Val Ser Arg Ala Thr Val
 1               5                  10                  15

Thr Ile Leu Leu Gly Ile Leu Phe Gly Phe Ser Ile Thr Tyr Tyr Leu
                20                  25                  30

Thr Ala Leu Lys Ser Leu Thr Asn Pro Ile Ile Cys Gly Pro Glu Gln
            35                  40                  45

Gln Ile Gly Gly Phe Asp Tyr Leu Asp Val Ile Ser Gln Arg Ala Asp
        50                  55                  60

Ala Asp Val Phe Thr Arg Ser Gln Ser Leu Pro Gly His Arg Arg Gly
 65                 70                  75                  80

Leu Ile Leu Val Ala Ile Met Thr Ala Ala Lys Tyr Val Asp Thr Arg
                85                  90                  95

Ala Tyr Asn Glu Leu Glu Ser Val His Glu Asp Met Pro Leu Ile Arg
            100                 105                 110

Leu Lys Gly Val Asp Asp Thr Tyr Pro Pro Gln Lys Lys Ser Phe Ala
        115                 120                 125

Met Val Lys Trp Leu Ala Glu Asn Met Ala Asp Glu Tyr Asp Trp Phe
    130                 135                 140

Leu Arg Ala Asp Asp Asp Leu Tyr Ile Arg Gly Glu Glu Leu Ala Leu
145                 150                 155                 160

Phe Leu Arg Ser Val Asp Ser Ser Lys Ala His Ile Ile Gly Gln Ala
                165                 170                 175

Gly Leu Gly Asn Ser Ala Glu Tyr Gly Leu Leu Ala Leu Gly Ser Thr
            180                 185                 190

Asp Asn Tyr Cys Met Gly Gly Pro Gly Ile Val Met Ser Arg Asp Thr
        195                 200                 205
```

```
Leu Leu Lys Val Ser Pro His Leu Glu Ser Cys Leu Gln His Met Leu
    210                 215                 220

Thr Ser His Glu Asp Val Glu Leu Gly Arg Cys Ile Arg Lys His Val
225                 230                 235                 240

Gly Val Ala Cys Thr Trp Asn Tyr Glu Met Gln Lys Leu Phe His Asn
                245                 250                 255

Asn Gln Ser Ala Ile Lys Glu Ser Tyr Ala Lys Asn Met Lys Glu Leu
            260                 265                 270

Lys Asp Ala Ile Thr Leu His Pro Ile Lys Asp Pro Ala Val Met Arg
        275                 280                 285

Lys Val His Leu Arg Asn Arg Glu Ile Lys Leu Arg Glu Ala Arg Ala
    290                 295                 300

Lys Arg Ser Leu Leu Ser Ser Glu Leu Ser Thr Ala Lys Ala Gln Thr
305                 310                 315                 320

Leu Val Arg Met Thr Pro Asn Arg Thr Asn Asp Leu Thr Pro Trp Glu
                325                 330                 335

Tyr Ile Asn Asn Asn Lys Ile Leu Phe Cys Ala Asp Arg Val Asn Cys
            340                 345                 350

Pro Arg His Thr Val Asp Leu Ser Ile Arg Thr Glu Met Ala Asp Thr
        355                 360                 365

Ile Thr Gln Leu Phe Asp Glu Phe Asn Thr Asn Ala Arg Gln Arg Gly
    370                 375                 380

Arg Val Leu Gln Phe Gln Ser Leu Gln Tyr Gly Tyr Met Arg Val Glu
385                 390                 395                 400

Pro Thr Lys Gly Val Asp Tyr Val Leu Asp Met Leu Leu Trp Phe Lys
                405                 410                 415

Lys Phe Arg Pro Pro Asn Arg Thr Thr Ile Ser Val Arg His Ala
            420                 425                 430

Tyr Val Gln Gln Thr Phe Gly Lys Leu Arg Ser Leu Ser Glu Gly Val
        435                 440                 445

Phe Arg Ser Asn Met Arg Ala Asn Ser Thr Leu Ile Glu Asp Pro Thr
    450                 455                 460

Leu His Met Ile Met Pro Leu Arg Gly Arg Ala Ala Ile Phe Ala Arg
465                 470                 475                 480

Phe Ala Gln His Leu Lys Ser Ile Cys Ala Arg Gly Gly Asp Leu
                485                 490                 495

Ala Val Ser Leu Thr Ile Val Leu Tyr Ser Ser Glu Asp Glu Met Glu
            500                 505                 510

Asn Arg Glu Thr Ile Glu Met Leu Arg Ala Ser Phe Ile Pro Val Thr
        515                 520                 525

Val Ile Glu Met Gly Asp Val Ser Phe Ser Arg Gly Val Ala Leu Met
    530                 535                 540

Arg Gly Ala Glu Thr Leu Pro Ala Asn Ala Leu Leu Phe Phe Thr Asp
545                 550                 555                 560

Val Asp Met Leu Phe Thr Cys Asp Ala Leu Lys Arg Ile Lys Ser Asn
                565                 570                 575

Thr Ile Leu Asn Ala Gln Ile Tyr Phe Pro Ile Val Phe Ser Glu Phe
            580                 585                 590

Ser His Glu Ser Trp Ser Glu Asn Asp Lys Leu Leu Ala Asp Ala Phe
        595                 600                 605

His Tyr Gly Arg Gly Arg Gly Tyr Phe Arg His Phe Gly Tyr Gly Leu
    610                 615                 620

Ala Ala Met Tyr Lys Ala Asp Leu Met Asp Val Gly Gly Phe Asp Thr
625                 630                 635                 640
```

Lys Ile Glu Gly Trp Gly Lys Glu Asp Val Asp Leu Phe Lys Ala
            645                 650                 655

Ile Lys Asn Gly Arg Leu Arg Val Ile Arg Val Pro Glu Pro Gly Leu
            660                 665                 670

Val His Ile Tyr His Pro Ile His Cys Asp Glu Asn Met Pro Thr Ala
            675                 680                 685

Gln Lys Asp Met Cys His Gly Ser Lys Ala Ala Ser Leu Ala Ser Ile
            690                 695                 700

Asp Thr Leu Val Glu Gln Ile Ala Gln Tyr Thr
705                 710                 715

<210> SEQ ID NO 6
<211> LENGTH: 788
<212> TYPE: PRT
<213> ORGANISM: Drosophila melanogaster

<400> SEQUENCE: 6

Met Thr Ala Lys Ser Phe Leu Glu Gly Arg Ala Arg Ala Val Tyr Asp
  1               5                  10                  15

Thr Trp Gly Lys Glu Val Pro Gly Arg Met Ala Phe Phe Ser Ser Glu
             20                  25                  30

Gly Ser Tyr Ser Asp Asp Leu Pro Val Val Gly Leu Lys Asn Val Asp
         35                  40                  45

Asp Arg Tyr Pro Pro Gln Lys Lys Ser Phe Met Met Leu Tyr Tyr Met
     50                  55                  60

Tyr Glu His Tyr Ile Asp Arg Phe Glu Trp Phe Ile Arg Ala Asp Asp
 65                  70                  75                  80

Asp Val Tyr Met Glu Pro Asp Lys Leu Glu Arg Phe Leu Arg Ser Ile
                 85                  90                  95

Asp Ser Ser Lys Pro Gln Phe Ile Gly Gln Ala Gly Lys Gly Asn Ser
            100                 105                 110

Glu Glu Phe Gly Leu Leu Ser Leu Glu Phe Asp Glu Asn Phe Cys Met
        115                 120                 125

Gly Gly Pro Gly Val Ile Leu Ser Ser Glu Thr Leu Arg Arg Val Ala
    130                 135                 140

Pro His Ile Pro Ser Cys Leu Lys Asn Leu Tyr Ser Thr His Glu Asp
145                 150                 155                 160

Val Glu Val Gly Arg Cys Val Gln Lys Phe Ala Gly Ile Pro Cys Thr
                165                 170                 175

Trp Asn Tyr Glu Met Gln Tyr Ile Leu Arg His Asn Ser Ser Gly Arg
            180                 185                 190

Asn Ala Tyr Thr Gly Lys Leu Lys Arg Lys Glu Ile His Asn Ala Ile
        195                 200                 205

Thr Leu His Pro Ile Lys Gln Ala Pro Leu Met Tyr Arg Leu His Ser
    210                 215                 220

Tyr Val Gln Gly Leu Lys Ala Glu Glu Met Arg Gln Glu Ser Leu Leu
225                 230                 235                 240

Leu His Arg Asp Ile Lys Arg Met Ala Lys Tyr Leu Glu Val Pro Asp
                245                 250                 255

Glu Ser Thr Tyr Met Leu Pro Ser Val Ser Pro Glu Ser Asp Ser Thr
            260                 265                 270

Lys Arg His Phe Gln Asp His Asn Ile Leu Gly Gly Trp His Asn Leu
        275                 280                 285

Lys Ile His Lys Ile His Lys Val Asp Arg Lys Ile Leu Thr Asn Leu
    290                 295                 300

```
Ala Ser Tyr Lys Asp Lys Gln Ile Gln Arg Ile Ser Pro Glu Leu Asn
305                 310                 315                 320

Lys Phe Val Pro Ala Ser Thr Asp Leu Leu Asp Trp Ser Phe Ile
            325                 330                 335

Ala Arg Ser Leu Tyr Ser Ala Ser Ala Asn Pro Lys Gln Lys Ile
            340                 345                 350

Asp Ser Ala Met Arg Glu Gly Leu Glu Asp Ala Ile Thr Glu Val Met
            355                 360                 365

Glu Asn Ile Asn Asn Tyr Ser Arg Gln Arg Gly Arg Val Ile Glu Phe
370                 375                 380

Arg Glu Leu Leu Tyr Gly Tyr His Arg Leu Asp Ala Leu His Gly Gln
385                 390                 395                 400

Asp Met Ile Leu Asp Leu Leu Ile Tyr Lys Lys Tyr Arg Gly Lys
            405                 410                 415

Lys Met Thr Val Pro Val Arg Arg His Leu Tyr Val Gln Arg Ala Phe
            420                 425                 430

Thr Gly Ile Phe Val Lys Glu Val Asp Glu Asp Phe Tyr Asn Val Thr
            435                 440                 445

Leu Gln Gln Ser Leu Leu Gly Ser Leu Phe Gln Asn Gly Met Ala Arg
450                 455                 460

Leu Ser Ser His Phe Thr Met Pro Ser Gly Leu Leu Ser Pro Thr Gln
465                 470                 475                 480

Asp Lys Ile Val Phe Val Leu Pro Ile Ala Gly Arg Leu Gly Thr Phe
            485                 490                 495

Glu Arg Phe Leu Arg Thr Tyr Glu Arg Val Cys Val Arg Gly Glu Gln
            500                 505                 510

His Cys Asp Leu Leu Val Val Ile Phe Gly Ser Pro Asp Glu Leu Gly
            515                 520                 525

Asp His Leu Gln Leu Leu His Asp Leu His Ala Arg His Val Tyr Gln
530                 535                 540

Gln Val Asn Trp Ile Gln Arg Ser Ser Ala Phe Ser Arg Gly Val Ala
545                 550                 555                 560

Leu Asp Val Ala Ala Arg Ser Ser Tyr Ile Arg Gln Glu Asp Ile Ile
            565                 570                 575

Leu Phe Ile Asp Val Asp Met Val Phe Glu Val Glu Thr Leu Gln Arg
            580                 585                 590

Val Arg Met His Thr Gln Arg Gly Lys Gln Val Tyr Leu Pro Ile Val
            595                 600                 605

Phe Ser Gln Tyr Asp Pro Gln Arg Arg Ser Gly Asp Ala Gly Gly Ser
610                 615                 620

Glu Asp Glu Gly Glu Thr Pro Arg Ile Asp Asp Glu Arg Gly Tyr Phe
625                 630                 635                 640

Arg Gln Phe Gly Phe Gly Ile Cys Ala Ile Tyr Lys Ser Asp Ile Leu
            645                 650                 655

Asp Glu Asp Ile Asn Gly Phe Asp Lys Asp Ile Thr Gly Trp Gly Leu
            660                 665                 670

Glu Asp Val Lys Phe Leu Glu Lys Ile Val Arg Val Gly Thr Arg Gln
            675                 680                 685

Arg Gly Phe Leu Ala Asn Thr Ala Glu Leu Ala Met Asp Tyr Asn Glu
            690                 695                 700

Ala Ala Glu Gln Trp Arg Arg Leu Ser Val Phe Arg Ala Pro Asp Pro
705                 710                 715                 720

Thr Leu Val His Ile Tyr His Asp Ile Ser Cys Asp Val Gln Leu Asp
```

```
                    725                 730                 735
Ala Pro Gln Tyr Asn Met Cys Leu Gly Thr Lys Ala Asn Ser Leu Gly
            740                 745                 750

Ser Thr Arg Leu Met Glu Gln Leu Phe His Ser Ser Pro Glu Asn Val
        755                 760                 765

Gln Phe Ala Ala Asp Phe Asn Arg Gln Lys Gln Gln Gln Gln Gln Gln
    770                 775                 780

Gln Gln Ala Arg
785
```